(12) United States Patent
Kamikawa et al.

(10) Patent No.: US 11,033,340 B2
(45) Date of Patent: Jun. 15, 2021

(54) MEDICAL SUPPORT ARM APPARATUS AND MEDICAL SYSTEM

(71) Applicant: SONY CORPORATION, Tokyo (JP)

(72) Inventors: Yasuhisa Kamikawa, Tokyo (JP); Tetsuharu Fukushima, Tokyo (JP); Wataru Kokubo, Tokyo (JP); Yasuhiro Matsuda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 286 days.

(21) Appl. No.: 15/762,600

(22) PCT Filed: Aug. 3, 2016

(86) PCT No.: PCT/JP2016/072827
§ 371 (c)(1),
(2) Date: Mar. 23, 2018

(87) PCT Pub. No.: WO2017/056704
PCT Pub. Date: Apr. 6, 2017

(65) Prior Publication Data
US 2018/0200006 A1    Jul. 19, 2018

(30) Foreign Application Priority Data
Oct. 1, 2015    (JP) .............................. JP2015-195904

(51) Int. Cl.
*A61B 34/30*    (2016.01)
*B25J 9/06*    (2006.01)
(Continued)

(52) U.S. Cl.
CPC .............. *A61B 34/30* (2016.02); *A61B 90/50* (2016.02); *B25J 9/0018* (2013.01); *B25J 9/06* (2013.01);
(Continued)

(58) Field of Classification Search
CPC . A61B 90/361; A61B 90/37; A61B 2090/372; A61B 2090/5025
See application file for complete search history.

(56) References Cited

U.S. PATENT DOCUMENTS 4,846,155 A * 7/1989 Kimura .............. A61B 1/00188
600/109
5,279,309 A * 1/1994 Taylor .................... A61B 34/20
600/595
(Continued)

FOREIGN PATENT DOCUMENTS

JP    62-61911 A    9/1994
JP    8-266555 A    10/1996
(Continued)

OTHER PUBLICATIONS

International Search Report dated Oct. 25, 2016 in PCT/JP2016/072827.

*Primary Examiner* — Timothy J Neal
*Assistant Examiner* — Jae Woo
(74) *Attorney, Agent, or Firm* — Xsensus LLP

(57) ABSTRACT

To make it possible to configure a medical support arm apparatus which does not impair operability for the surgeon, and which is also compact. Provided is a medical support arm apparatus including: an arm section configured so that a medical tool is provided on a front end, and movable axes are arranged so that the arm section has at least six degrees of freedom. Among the movable axes, a movable axis provided on the front end side that prescribes an attitude of the medical tool is a passive axis that rotates by following an external force, and at least one axis provided on a base end side that prescribes a position of the medical tool is a drive axis driven by an actuator.

9 Claims, 10 Drawing Sheets

(51) Int. Cl.
  *A61B 90/50* (2016.01)
  *B25J 9/00* (2006.01)
  *A61B 90/00* (2016.01)

(52) U.S. Cl.
  CPC ............. *A61B 90/361* (2016.02); *A61B 90/37* (2016.02); *A61B 2090/372* (2016.02); *A61B 2090/5025* (2016.02)

(56) References Cited

U.S. PATENT DOCUMENTS

| | | | | |
|---|---|---|---|---|
| 5,835,693 | A * | 11/1998 | Lynch | G06T 13/20 345/473 |
| 7,107,090 | B2 * | 9/2006 | Salisbury, Jr. | A61B 1/313 600/102 |
| 2004/0111183 | A1 * | 6/2004 | Sutherland | A61B 34/77 700/245 |
| 2004/0138524 | A1 * | 7/2004 | Ueda | A61B 90/50 600/102 |
| 2004/0172012 | A1 * | 9/2004 | Otsuka | A61B 90/50 606/1 |
| 2009/0062813 | A1 | 3/2009 | Giuseppe et al. | |
| 2011/0268254 | A1 * | 11/2011 | Peters | A61B 6/4441 378/197 |
| 2012/0220428 | A1 * | 8/2012 | Carlson | A63B 21/156 482/8 |
| 2012/0300909 | A1 * | 11/2012 | Simmons | A61B 6/4441 378/194 |
| 2014/0052153 | A1 * | 2/2014 | Griffiths | A61B 34/70 606/130 |
| 2014/0052298 | A1 * | 2/2014 | Hourtash | B25J 9/1689 700/263 |
| 2014/0107665 | A1 * | 4/2014 | Shellenberger | A61B 34/70 606/130 |
| 2014/0135794 | A1 * | 5/2014 | Cau | A61B 34/75 606/130 |
| 2015/0090065 | A1 * | 4/2015 | Kishi | A61B 34/37 74/491 |
| 2015/0250547 | A1 * | 9/2015 | Fukushima | B25J 9/1697 606/130 |
| 2015/0321355 | A1 * | 11/2015 | Kishi | B25J 9/1697 606/130 |
| 2019/0328475 | A1 * | 10/2019 | Arai | A61B 34/30 |
| 2020/0129052 | A1 * | 4/2020 | Unai | A61B 90/50 |

FOREIGN PATENT DOCUMENTS

| | | |
|---|---|---|
| JP | 2005-224368 A | 8/2005 |
| JP | 2015-521086 A | 7/2015 |
| WO | WO 2014/028557 A1 | 2/2014 |
| WO | WO 2014/028699 A1 | 2/2014 |
| WO | WO 2014/084408 A1 | 6/2014 |

* cited by examiner

MEDICAL SUPPORT ARM APPARATUS AND MEDICAL SYSTEM

TECHNICAL FIELD

The present disclosure relates to a medical support arm apparatus and a medical system.

BACKGROUND ART

Recently, in the medical field, support arm apparatuses are being used to support surgeries. For example, a method is proposed in which an imaging section including a camera or the like is provided on the front end of an arm section of a support arm apparatus, and the surgeon performs surgery while looking at a picture taken by the imaging section. Alternatively, there is also proposed a method in which a treatment tool such as forceps or a retractor is provided on the front end of the arm section, and the support arm apparatus is made to support or perform operations with the treatment tool which has performed manually in the past.

Generally, to control with high precision the position and the attitude of a medical tool (such as the imaging section and the treatment tool described above) provided on the front end of the arm section, and also in consideration of operability for the surgeon when causing the medical tool to move, the arm section of a support arm apparatus is configured so that the weight of the arm section may be supported. For example, a method is known whereby a counterweight is provided on the base end side of the arm section so that the arm section is balanced overall (that is, so that the weight of the arm section itself may be supported), and the support arm apparatus is configured as what is called a balance arm (for example, see Patent Literature 1).

CITATION LIST

Patent Literature

Patent Literature 1: JP H8-266555A

DISCLOSURE OF INVENTION

Technical Problem

However, since a counterweight is relatively bulky, if the support arm apparatus is configured as a balance arm, the apparatus as a whole also becomes bulky. Consequently, the space of the operating room becomes dominated by the support arm apparatus, and the surgical work may be impeded. Also, since the weight of the apparatus as a whole becomes heavier, for example, in the case of configuring the support arm apparatus so that the arm section hangs down from the ceiling, large-scale construction work becomes necessary, and there is a risk of increased costs for installation. Furthermore, generally, since the inertia is also large for a support arm apparatus provided with a counterweight, rapidly and comfortably operating the front end of the arm section tends to be difficult.

Accordingly, the present disclosure proposes a new and improved medical support arm apparatus which can be configured not to impair operability for the surgeon and also compactly, as well as a medical system provided with such a medical support arm apparatus.

Solution to Problem

According to the present disclosure, there is provided a medical support arm apparatus including: an arm section configured so that a medical tool is provided on a front end, and movable axes are arranged so that the arm section has at least six degrees of freedom. Among the movable axes, a movable axis provided on the front end side that prescribes an attitude of the medical tool is a passive axis that rotates by following an external force, and at least one axis provided on a base end side that prescribes a position of the medical tool is a drive axis driven by an actuator.

In addition, according to the present disclosure, there is provided a medical system including: an observation apparatus configured to take an image of an operating site for observing the operating site; and a display apparatus configured to display the taken image. The observation apparatus includes an arm section configured so that an imaging section that takes the image is provided on a front end, and movable axes are arranged so that the arm section has at least six degrees of freedom, and in the arm section, among the movable axes, a movable axis provided on the front end side that prescribes an attitude of the imaging section is a passive axis that rotates by following an external force, and at least one axis provided on a base end side that prescribes a position of the imaging section is a drive axis driven by an actuator.

According to the present disclosure, for the movable axes provided in the arm section of the medical support arm apparatus, at least one movable axis provided on the base end side that prescribes the position of the medical tool is configured as a drive axis. According to the configuration, by driving the drive axis to support the weight of the configuration on the front end side, it becomes possible to maintain the position and the attitude of the arm section, without providing a counterweight. Consequently, a medical support arm apparatus which is more compact and which also does not impair operability for the surgeon may be realized.

Advantageous Effects of Invention

According to the present disclosure as described above, it is possible to configure a medical support arm apparatus which does not impair operability for the surgeon, and which is also compact. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
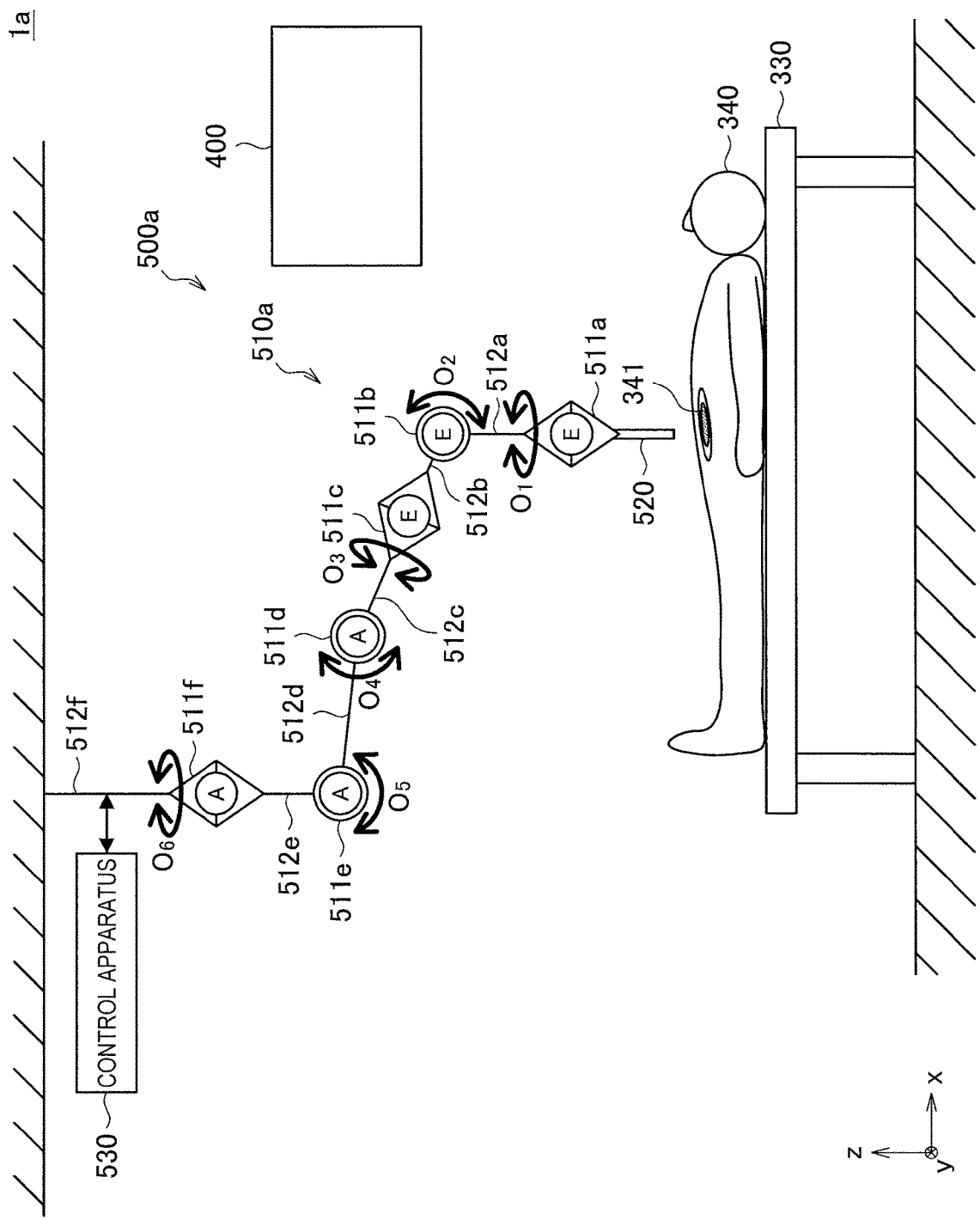
FIG. 1 is a diagram illustrating a schematic configuration of a medical system and a support arm apparatus according to a first embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.
1. First embodiment
1-1. Configuration of system and support arm apparatus
1-2. Configuration of joint sections and operation of arm section
2. Second embodiment
2-1. Configuration of system and support arm apparatus
3. Third embodiment
3-1. Configuration of system and support arm apparatus
4. Fourth embodiment
4-1. Configuration of system and support arm apparatus
5. Fifth embodiment
5-1. Configuration of system and support arm apparatus
6. Sixth embodiment
6-1. Configuration of system and support arm apparatus
7. Seventh embodiment
7-1. Configuration of system and support arm apparatus
8. Conclusion
9. Supplement

1. First Embodiment (1-1. Configuration of System and Support Arm Apparatus)

Referring to FIG. 1, the configuration of the medical system and the support arm apparatus according to the first embodiment of the present disclosure will be described. FIG. 1 is a diagram illustrating a schematic configuration of a medical system and a support arm apparatus according to the first embodiment.

Referring to FIG. 1, the medical system 1a according to the first embodiment includes a support arm apparatus 500a and a display apparatus 400. In FIG. 1, a state is illustrated in which the support arm apparatus 500a is used to perform surgery on a patient 340 on top of an operating table 330. Specifically, in surgery using the support arm apparatus 500a, a picture of an operating site 341 of the patient 340 is taken by an imaging section 520 of the support arm apparatus 500a described later, and the taken picture is displayed on the display apparatus 400 provided inside the operating room. The surgeon (not illustrated) performs various treatments on the operating site 341 while observing the state of the operating site 341 through the picture appearing on the display apparatus 400. In this way, the medical system 1a is a system for supporting the surgeon (user) during surgery.

(Display Apparatus 400)

The display apparatus 400 is an apparatus that displays various information in various formats such as text and images on a display screen, and thereby visually notifies the user of the various information. As above, the display apparatus 400 is installed inside the operating room, and displays a picture of the operating site 341 taken by the imaging section 520 of the support arm apparatus 500a.

For example, the display apparatus 400 includes functions such as an image signal processing section (not illustrated) that performs various types of image processing on a picture signal acquired by the imaging section 520, and a display control section (not illustrated) that controls the displaying of a picture based on the processed picture signal on the display screen. Otherwise, the display apparatus 400 may include any of various functions included in a typical display apparatus.

Specifically, any of various known types of display apparatus may be used as the display apparatus 400, such as a cathode ray tube (CRT) display apparatus, a liquid crystal display apparatus, a plasma display apparatus, or an electroluminescence (EL) display apparatus. Also, communication between the imaging section 520 and the display apparatus 400 may be realized by any of various known types of wired or wireless methods.

(Support Arm Apparatus)

The support arm apparatus 500a is provided with an arm section 510a, the imaging section 520 attached to the front end of the arm section 510a, and a control apparatus 530 that controls the operation of the support arm apparatus 500a. The support arm apparatus 500a is a medical support arm apparatus 500a which is provided inside an operating room and which supports the execution of a surgery by a surgeon.

The arm section 510a has a base end section attached to the ceiling of the operating room, and is installed to hang down from the ceiling. Note that FIG. 1 illustrates the control apparatus 530 schematically, but in actuality, the control apparatus 530 may be provided at the connection site between the base end section of the arm section 510a and the ceiling, may be installed in a location (for example, on the floor of the operating room) at a distance from the arm section 510a, or may be provided to be communicable connected to the arm section 510a by any of various types of wired or wireless communication methods.

Note that in the following, when describing the configuration of the arm section 510a, the side on which the imaging section 520 is provided may also be called the front end side, the front end section, or the like, while the side near the ceiling may also be called the base end side, the base end section, or the like. Also, the vertical direction is also called the z-axis direction, while the two directions mutually orthogonal to the z-axis direction (that is, the two directions mutually orthogonal in the horizontal plane) are also called the x-axis direction and the y-axis direction, respectively.

The arm section 510a includes joint sections 511a, 511b, 511c, 511d, 511e, and 511f respectively provided at positions corresponding to each rotation axis (called the first axis $O_1$, the second axis $O_2$, the third axis $O_2$, the fourth axis $O_4$, the fifth axis $O_5$, and the sixth axis $O_6$ in order from the front end side), and multiple links 512a, 512b, 512c, 512d, 512e, and 512f rotatably joined to each other by the joint sections 511b to 511f. Also, on the front end of the arm section 510a, the imaging section 520 is attached via the joint section 511a.

Note that although illustrated simply by solid lines in FIG. 1, in actuality, the links 512a to 512f may be rod-shaped or tube-shaped members having a predetermined thickness. Also, the cross-sectional shapes of the links 512a to 512f are not limited, and may be any of various types of shapes, such as circular, elliptical, or rectangular. As a specific structure of the links 512a to 512f, any of various types used as the links of a typical support arm apparatus may be applied.

Also, although illustrated simply by combinations of circles and triangles in FIG. 1, in actuality, the joint sections 511a to 511f have shafts that act as rotation axes, bearings that pivotally support the shafts, and the like, and may be members enabling the rotation of one member about another member. However, as described later, the first embodiment has a characteristic arrangement of actuators and rotary encoders (hereinafter simply called encoders) provided with respect to the joint sections 511a to 511f. In the first embodiment, it is sufficient for the joint sections 511a to 511f to be configured enabling the rotation of one member about another member, and also enabling the realization of the arrangement of the actuators and encoders described later, whereas for the rest of the specific structure, any of various types used as the joint sections of a typical support arm apparatus may be applied.

The configuration of the arm section 510a will be described in detail. The base end of the link 512f that extends in an approximately vertical direction is attached to the ceiling. The front end of the link 512f is joined to the base end of the link 512e through the joint section 511f, and the link 512f rotatably supports the link 512e through the joint section 511f.

Thereafter, similarly, the front ends of the links 512e, 512d, 512c, and 512b are joined to the base ends of the links 512d, 512c, 512b and 512a through the joint sections 511e, 511d, 511c, and 511b, respectively. In addition, the links 512e, 512d, 512c, and 512b rotatably support the links 512d, 512c, 512b, and 512a through the joint sections 511e, 511d, 511c, and 511b, respectively.

The imaging section 520 is joined to the front end of the link 512a through the joint section 511a. The link 512a rotatably supports the imaging section 520 through the joint section 511a.

In this way, the base end of the link 512f connected to the ceiling acts as a fulcrum, and ends of the multiple links 512a to 512f are joined to each other by the joint sections 511b to 511f, thereby forming an arm shape extending from the ceiling.

Among the rotation axes, the first axis $O_1$, the third axis $O_2$, and the sixth axis $O_6$ are rotation axes in a direction approximately parallel to the extension direction of the links 512a, 512c, and 512f provided on the base end side. In this specification, the rotation axes having such a direction are also called the yaw axes for convenience. On the other hand, the second axis $O_2$, the fourth axis $O_4$, and the fifth axis $O_5$ are rotation axes in a direction approximately orthogonal to the extension direction of the links 512b, 512d, and 512e provided on the base end side. In this specification, the rotation axes having such a direction are also called the pitch axes for convenience.

In other words, the arm section 510a is an arrangement of, from the base end side, a yaw axis (the sixth axis $O_6$), a pitch axis (the fifth axis $O_5$), a pitch axis (the fourth axis $O_4$), a yaw axis (the third axis $O_3$), a pitch axis (the second axis $O_2$), and a yaw axis (the first axis $O_1$), in that order. With this configuration, in the arm section 510a, three degrees of translational freedom and three degrees of rotational freedom, for a total of six degrees of freedom, are realized with respect to the motion of the imaging section 520. By configuring the arm section 510a to have six degrees of freedom, it becomes possible to move the imaging section 520 freely inside the movable range of the arm section 510a.

However, the configuration of the arm section 510a is not limited to the illustrated example. In the first embodiment, it is sufficient for the arm section 510a to be configured to have at least six degrees of freedom with respect to the motion of the imaging section 520, and the numbers and arrangement of the joint sections 511a to 511f and the links 512a to 512f, the directions of the drive axes of the joint sections 511a to 511f, the lengths of the links 512a to 512f, and the like may be set appropriately so that the arm section 510a has the desired degrees of freedom equal to or greater than six degrees of freedom.

Herein, although described later in detail in (1-2. Configuration of joint sections and operation of arm section) below, in the first embodiment, only some of these rotation axes are configured as drive axes driven by actuators. Additionally, the other rotation axes are configured as passive axes that rotate by following an external force. The external force is, for example, a force imparted to a passive axis in relation to the rotation of a drive axis, or a force imparted to a passive axis in accordance with an operation of the surgeon attempting to move the imaging section 520.

The actuators include at least a motor that produces a driving force, a rotary encoder (hereinafter simply called an encoder) that detects the rotational angle for a rotation axis, and a torque sensor that detects the force (torque) acting on a joint section. The driving of the actuators is controlled by the control apparatus 530. By having the control apparatus 530 control the driving of each actuator provided with respect to each drive axis, rotation in each drive axis is controlled, and the driving of the arm section 510a, such as extending or contracting (folding up) the arm section 510a, for example, is controlled.

The imaging section 520 is an example of an observation unit for observing an operating site, and includes a camera or the like capable of photographing a moving image and/or a still image of a photographic target, for example. The imaging section 520 may be what is known as a video microscope.

When performing surgery, the position and the attitude of the arm section 510a and the imaging section 520 are controlled so that the imaging section 520 provided on the front end of the arm section 510a photographs the operating site 341 of the patient 340. A picture signal regarding the operating site 341 photographed by the imaging section 520 is transmitted to the display apparatus 400. On the basis of the transmitted picture signal, a picture of the operating site 341 is displayed on the display apparatus 400. The surgeon performs surgery while observing the operating site 341 by the picture appearing on the display apparatus 400.

Note that for the specific configuration of the imaging section 520, any of various known types of video microscope configurations may be applied. For example, although illustrated simply as a rod-shaped member in FIG. 1, in actuality, the imaging section imaging section 520 may include a cylindrical housing, an image sensor which is provided inside the housing, and which receives light (observation light) from a photographic target and outputs a picture signal corresponding to the observation light, and an optical system which is also provided inside the housing and which condenses the observation light onto the image sensor. An opening is provided in the bottom end section of the cylindrical housing, and an objective lens is disposed in the opening. Observation light enters into the housing through the objective lens, and by condensing the light onto the image sensor by the optical system, a picture signal expressing an image of the photographic target (for example, the operating site 341) may be acquired by the image sensor.

Also, the imaging section 520 may be provided with a function that adjusts the magnification and focus by appropriately moving a zoom lens and a focus lens included in the optical system. By displaying a picture of the operating site 341 appropriately enlarged and taken by the imaging section 520 on the display apparatus 400, the surgeon becomes able to perform enlarged observation of the operating site 341. The adjustment of the magnification and focus in the imaging section 520 may be executed manually by the surgeon through an input apparatus (not illustrated) provided on the support arm apparatus 500a, or may be executed automatically by using a typical autofocus function (AF function) or the like, for example. Otherwise, the imaging section 520 may be provided with any of various types of functions included in a typical video microscope.

Herein, the support arm apparatus 500a provided with an observation unit for observing an operating site of a patient on the front end of the arm section 510a like the support arm apparatus 500 is also called the observation apparatus 500a in this specification. In the illustrated example, the imaging section 520 is provided as the observation unit, but the observation unit is not limited to such an example, and an endoscope, an optical microscope, or the like may be provided as the observation unit, for example.

However, the unit provided on the front end of the arm section 510a is not limited to an observation unit, and any of various types of medical tools may be attached to the front end of the arm section 510a. For example, on the front end of the arm section 510a, any of various types of treatment tools, such as forceps or a retractor, may be connected. Alternatively, a light source for an endoscope or a microscope, or a surgical energy device used to seal blood vessels, for example, may be connected on the front end of the arm section 510a.

The control apparatus 530 includes a processor such as a central processing unit (CPU) or a digital signal processor (DSP), or a microcontroller, control board, or the like on which these processors and a storage element such as memory are mounted. By having a processor of the control apparatus 530 execute signal processing following a predetermined program, the operation of the support arm apparatus 500a is controlled.

In the first embodiment, force control is used favorably as the control method of the support arm apparatus 500a. With force control, the state (position, attitude, acting force, and the like) of the arm section 510a and the imaging section 520 is detected by the encoder and/or torque sensor provided in each of the joint sections 511a to 511f. In addition, on the basis of the detected state of the arm section 510a and the imaging section 520, a generated torque in the drive axes necessary to cause the arm section 510a to execute a desired operation is computed. By driving the actuators provided with respect to the drive axes so that the computed generated torque is generated, the operation of the arm section 510a is controlled to execute the desired operation. The desired operation may be, for example, a gravity compensation operation, a position fine movement operation, a pivot operation, and the like (the details of these operations will be further described later).

With force control, the driving of the actuators and the operation of the arm section 510a may be controlled by the control apparatus 530 in response to an operation in which the surgeon touches the arm section 510a directly to move the arm section 510a, for example, so that the arm section 510a moves in the direction of a force imparted to the arm section 510a (in other words, to track the operation of the surgeon). In this way, by using force control, the surgeon is able to move the arm section 510a while touching the arm section 510a directly, thereby making easier and more intuitive operations possible. Note that in the following description, an operation in which the surgeon moves the arm section 510a while touching the arm section 510a directly will also be called a direct operation.

However, the first embodiment is not limited to such an example, and position control may also be used as the control method of the support arm apparatus 500a. In the case in which the support arm apparatus 500a is controlled by position control, the support arm apparatus 500a may be provided with an input apparatus for operating the arm section 510a. The surgeon is able to move the arm section 510a through the input apparatus.

Note that as a specific driving method of the arm section 510a by force control or position control, any of various known types of methods may be used, and thus a detailed description is omitted herein.

(1-2. Configuration of Joint Sections and Operation of Arm Section)

As described with reference to FIG. 1, the arm section 510a is an arrangement of, from the base end side, a yaw axis (the sixth axis $O_6$), a pitch axis (the fifth axis $O_5$), a pitch axis (the fourth axis $O_4$), a yaw axis (the third axis $O_3$), a pitch axis (the second axis $O_2$), and a yaw axis (the first axis $O_1$), in that order.

Consequently, in the arm section 510a, by controlling the rotation about the first axis $O_1$, the facing of the picture photographed by the imaging section 520 is controlled. Also, by controlling the rotation about the second axis $O_2$, the facing of the imaging section 520 in the x-z plane is controlled. Also, by controlling the rotation about the third axis $O_3$, the facing of the imaging section 520 in the y-z plane is controlled. In other words, the first axis $O_1$, the second axis $O_2$, and the third axis $O_3$ may be said to be rotation axes that prescribe the facing of the optical axis of the imaging section 520, or in other words, the attitude of the imaging section 520.

On the other hand, by controlling each of the rotations about the fourth axis $O_4$, the fifth axis $O_5$, and the sixth axis $O_6$, the position of the imaging section 520 in three-dimensional space is controlled. In other words, the fourth axis $O_4$, the fifth axis $O_5$, and the sixth axis $O_6$ may be said to be rotation axes that prescribe the position of the imaging section 520.

In this way, in the arm section 510a of the support arm apparatus 500a, on the front end side, a rotation axis that may prescribe the attitude of the unit provided on the front end is arranged, while on the base end side, a rotation axis that may prescribe the position of the unit is arranged. Note that such an arrangement of rotation axes is not unique to the first embodiment, and is also widely applied in typical support arm apparatus.

In the first embodiment, among the first axis $O_1$ to the sixth axis $O_6$, the rotation axes which are provided on the base end side and which may prescribe the position of the imaging section 520, namely the fourth axis $O_4$ to the sixth axis $O_6$, are configured as drive axes. In other words, actuators are provided in the joint sections 511d to 511f corresponding to these rotation axes.

Also, the rotation axes which are provided on the front end side and which may prescribe the attitude of the imaging section 520, namely the first axis $O_1$ to the third axis $O_3$, are configured as passive axes. The joint sections 511a to 511c corresponding to these rotation axes are not provided with actuators, and are provided with encoders only.

Note that in FIG. 1, for the sake of comprehension, the joint sections 511d to 511f provided with actuators are denoted with "A" and the joint sections 511a to 511c provided with encoders only are denoted with "E", thereby indicating the arrangement of the actuators and the encoders.

According to the configuration, by appropriately controlling the driving of the actuators provided in the joint sections 511d to 511f with the control apparatus 530, the arm section 510a is capable of executing a gravity compensation operation, a position fine movement operation, and a pivot operation.

The gravity compensation operation refers to an operation of supporting, with any of the actuators, the weight of the configuration of the arm section 510a farther on the front end side than the joint sections provided with the actuators (that is, the joint sections corresponding to any of the drive axes). During the gravity compensation operation, to support the weight, the drive axes which are pitch axes are driven. According to the first embodiment, the actuators provided on the joint sections 511d and 511e corresponding to the drive axes which are pitch axes (the fourth axis $O_4$ and the fifth axis $O_5$) are driven to support the weight of the configuration farther on the front end side than the joint section 511d (that is, the link 512c, the joint section 511c, the link 512b, the joint section 511b, the link 512a, the joint section 511a, and the imaging section 520), thereby realizing the gravity compensation operation.

Specifically, in the gravity compensation operation, by the encoders provided in the joint sections 511a to 511c, the rotational angles in these joint sections 511a to 511c are detected. The control apparatus 530 computes the current center-of-gravity position of the configuration on the front end side, on the basis of the detected rotational angles. Additionally, on the basis of the computed center-of-gravity position of the configuration on the front end side, the control apparatus 530 calculates the moment imposed on the base end side by the configuration on the front end side, and drives the actuators provided in the joint sections 511d and 511e so that a torque canceling out the moment is generated.

Note that an internal model of the arm section 510a input in advance into the control apparatus 530 includes information about the weight of the configuration on the front end side, as information about the structure of the arm section 510a. Consequently, the control apparatus 530 is able to calculate the above moment on the basis of the information about the computed center-of-gravity position of the configuration on the front end side and the information about the weight of the configuration on the front end side.

By performing the gravity compensation operation, in the arm section 510a, it becomes possible to maintain the position and attitude, even if a counterweight is not provided. Consequently, a more compact and lightweight support arm apparatus 500a may be realized.

Herein, to perform the gravity compensation operation, it is sufficient to be able to support the weight of the configuration on the front end side of the arm section 510a at any joint section farther on the base end side. Thus, among the rotation axes provided in the arm section 510a, it is sufficient to configure at least axis relatively on the base end side as a drive axis. For example, favorably, at least one axis among the three axes (the fourth axis $O_4$ to the sixth axis $O_6$) that may prescribe the position of the imaging section 520 may be configured as a drive axis. In other words, the configuration of the arm section 510a that may realize the gravity compensation operation is not necessarily limited to one according to the first embodiment, and may be another configuration if the above conditions are satisfied. For example, the support arm apparatus 500b, 500c, 500d, 200a, 200b, and 200c according to the second to seventh embodiments described later may satisfy the above conditions, and the gravity compensation operation is realizable.

Also, the position fine movement operation refers to an operation of translating the imaging section 520 a tiny amount in the x-axis direction, the y-axis direction, or the z-axis direction, in accordance with an operation of the surgeon. For example, in the case in which the imaging section 520 is enlarging and photographing a tiny site, even if the imaging section 520 moves just slightly, the observation range moves greatly. Consequently, in the case of wanting to move the observation range slightly, it is necessary to move the imaging section 520 by an extremely small amount. In this case, even if the arm section 510a is put into a completely freely movable state and the surgeon attempts to adjust the position of the imaging section 520, it is difficult to move the imaging section 520 slightly to the desired position. Accordingly, by executing the position fine movement operation, the imaging section 520 can be moved slightly, making it possible to move the observation range more easily.

Note that in the case in which force control is applied as the control method of the support arm apparatus 500a, the position fine movement operation may be executed in accordance with a direct operation by the surgeon, while in the case in which position control is applied as the control method of the support arm apparatus 500a, the position fine movement operation may be executed in accordance with an operation input by the surgeon through an input apparatus such as a lever or directional keys. In the case of the former, the force imparted by the surgeon attempting to move the arm section 510a or the imaging section 520 is detected by the torque sensors of the actuators of the drive axes, the actuators are driven by the control apparatus 530 and the motion of the arm section 510a is controlled so that the imaging section 520 moves finely in the direction of the force. On the other hand, in the case of the latter, the actuators are driven by the control apparatus 530 and the motion of the arm section 510a is controlled so that the imaging section 520 moves finely in the direction input by the surgeon through the input apparatus.

Herein, to perform the position fine movement operation, it is necessary for the position of the imaging section 520 to be movable by the driving of the actuators, and thus it is sufficient for at least the three axes (the fourth axis $O_4$ to the sixth axis $O_6$) that may prescribe the position of the imaging section 520 to be configured as drive axes. In other words, the configuration of the arm section 510a that may realize the position fine movement operation is not necessarily limited to one according to the first embodiment, and may be another configuration if the above conditions are satisfied. For example, the support arm apparatus 200b and 200c according to the sixth and seventh embodiments described later may satisfy the above conditions, and the position fine movement operation is realizable.

Also, the pivot operation refers to an operation in which the imaging section 520 moves while the optical axis of the imaging section 520 is facing a predetermined point in space, and in addition, the imaging section 520 maintains a fixed distance to the predetermined point. The above predetermined point that acts as the point of reference for the pivot operation is also called the pivot point. For example, in the state of setting the pivot point to the operating site 341, a pivot operation, for example, the imaging section 520 can be moved while always facing the operating site 341 and also while maintaining a fixed distance to the operating site 341, thereby making it possible to observe the operating site 341 from various angles, convenience is improved for the surgeon.

Herein, processes in the control apparatus 530 during the pivot operation will be described in detail. When the surgeon moves the imaging section 520, the pivot operation is realized by the control apparatus 530 controlling the rotational angles of the fourth axis $O_4$ to the sixth axis $O_6$ so that the imaging section 520 moves while the optical axis of the imaging section 520 is facing in the direction of the observation site, and in addition, while maintaining a fixed distance between the imaging section 520 and the observation site. In other words, during the pivot operation, the rotational angles of the passive axes, namely the first axis $O_1$ to the third axis $O_3$ (that is, the attitude of the configuration on the front end side) are determined in accordance with a user operation, the rotational angles of the fourth axis $O_4$ to the sixth axis $O_6$ are determined so that the pivot operation may be realized by the control apparatus 530 in accordance with the attitude of the configuration on the front end side, and as a result, the rotational angles in all of the rotation axes are uniquely determined.

Figure 2:
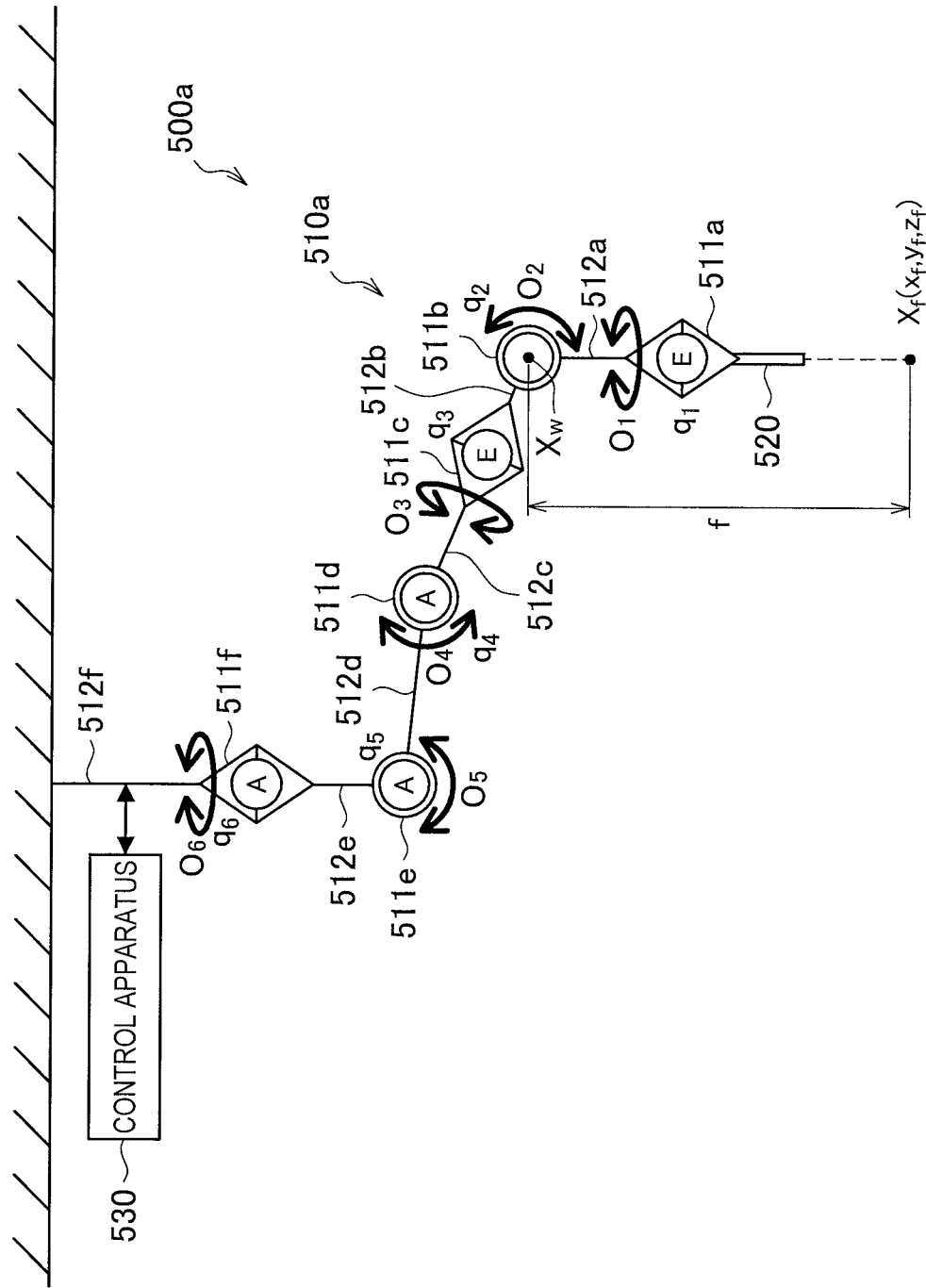
FIG. 2 is an explanatory diagram for explaining processes in a control apparatus during a pivot operation.
Figure 3:
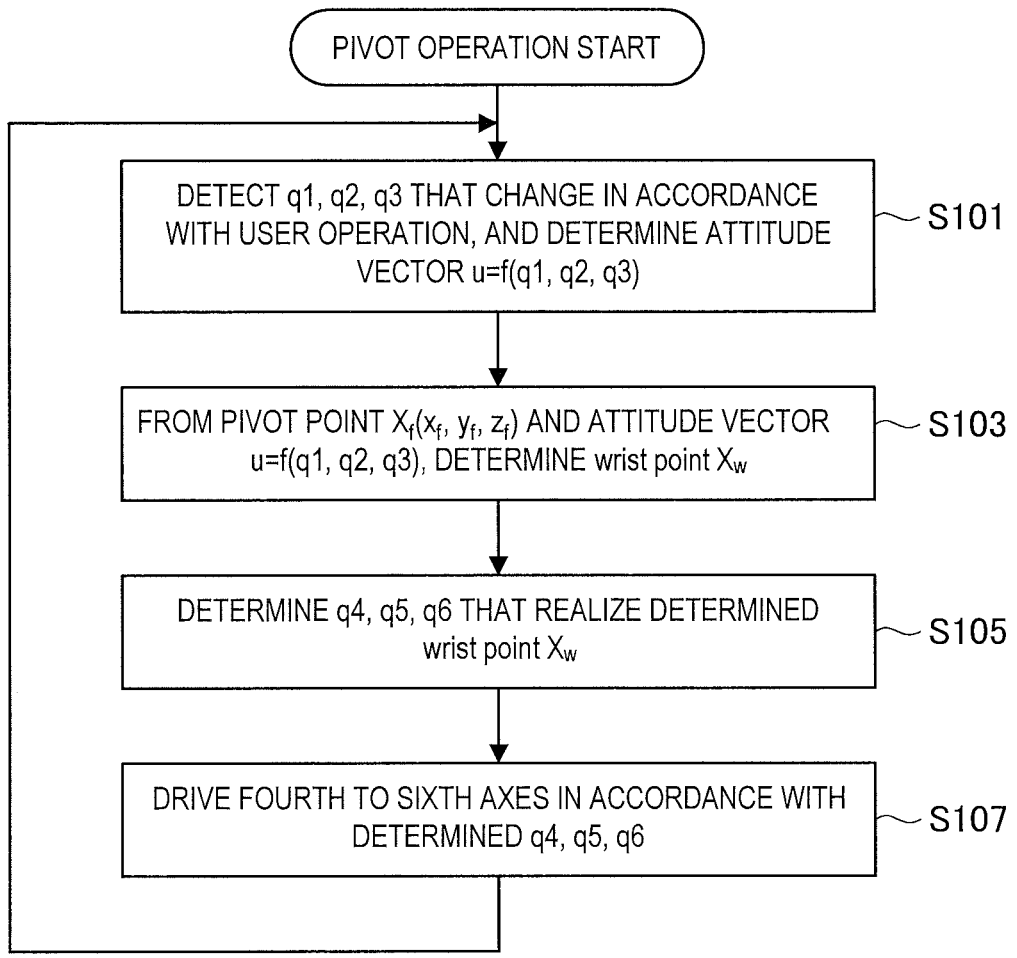
FIG. 3 is a flowchart illustrating an example of a processing sequence in a control apparatus during a pivot operation.

FIGS. 2 and 3 will be referenced to describe processes in the control apparatus 530 during the pivot operation. FIG. 2 is an explanatory diagram for explaining processes in the control apparatus 530 during the pivot operation. Note that in FIG. 2, only the support arm apparatus 500a is extracted from FIG. 1 and illustrated. FIG. 3 is a flowchart illustrating an example of a processing sequence in the control apparatus 530 during the pivot operation. Note that each process illustrated in FIG. 3 is executed by having a processor of the control apparatus 530 operate in accordance with a predetermined program.

As illustrated in FIG. 2, the rotational angles for the first axis $O_1$ to the sixth axis $O_6$ are taken to be q1 to q6. Also, the pivot point is placed at $X_f=(x_f, y_f, z_f)$. The pivot point $X_f$ is the operating site 341 of the patient 340, for example. Also, the configuration between the joint sections 511a to 511c corresponding to the first axis $O_1$ to the third axis $O_3$ is the part corresponding to what may be called the wrist section, and the center-of-gravity-position (wrist point) of the wrist section is taken to be $X_w$. Furthermore, a vector expressing the attitude of the wrist section, namely an attitude vector v, is expressed u=f(q1, q2, q3), as a function of the three rotational angles q1 to q3 of the first axis $O_1$ to the third axis $O_3$.

During the pivot operation, the pivot point $X_f$, and the distance f from the pivot point $X_f$ to the wrist point $X_w$, are preset. In other words, during the pivot operation, the control apparatus 530 obtains information about the coordinates ($x_f$, $y_f$, $z_f$) of the pivot point $X_f$ in space, and the distance f from the pivot point $X_f$ to the wrist point $X_w$.

Referring to FIG. 3, during the pivot operation, first, the rotational angles q1, q2, and q3 of the first axis $O_1$ to the third axis $O_3$ that change in accordance with a user operation are detected, and the attitude vector u=f(q1, q2, a3) is determined (step S101). Specifically, the rotational angles q1, q2, and q3 are detected by the encoders provided in the joint sections 511a to 511c. The detection values (q1, q2, q3) of the rotational angles by each of the encoders are transmitted to the control apparatus 530, and in the control apparatus 530, the attitude vector u is calculated on the basis of these detection values.

Next, the wrist point $X_w$ is determined from the pivot point $X_f$ ($x_f, y_f, z_f$) and the attitude vector u=f(q1, q2, q3) (step S103). Herein, typically, in an arm section configured to have six degrees of freedom, for a single attitude vector u, the wrist point $X_w$ at which the distance from a predetermined pivot point $X_f$ is f may be uniquely determined. As described above, since the arm section 510a of the support arm apparatus 500a is configured to have six degrees of freedom, in the first embodiment, in step S103, the wrist point $X_w$ is determined uniquely.

Next, the rotational angles q4, q5, and q6 of the fourth axis $O_4$ to the sixth axis $O_6$ are determined so as to realize the determined wrist point $X_w$ (step S105). Since the wrist point $X_w$ is uniquely determined, the rotational angles q4, q5, and q6 to realize it may be uniquely determined.

Additionally, in accordance with the determined rotational angles q4, q5, and q6, the fourth axis $O_4$ to the sixth axis $O_6$ are driven, or in other words, the actuators provided in the joint sections 511d to 511f are driven (step S107). With this arrangement, the pivot operation may be realized.

Herein, to realize the pivot operation, it is sufficient for the arm section 510a to be configured so that the rotational angles q1 to q6 of all of the first axis $O_1$ to the sixth axis $O_6$ included in the arm section 510a are detectable or controllable, and also so that the coordinates of the wrist point $X_w$ in space may be determined uniquely when the pivot point $X_f$, the attitude vector u, and the distance f between the pivot point $X_f$ and the wrist point $X_w$ are fixed. In other words, the configuration of the arm section 510a that may realize the pivot operation is not necessarily limited to one according to the first embodiment, and may be another configuration if the above conditions are satisfied. For example, the support arm apparatus 200b and 200c according to the sixth and seventh embodiments described later may satisfy the above conditions, and the pivot operation is realizable.

Note that when performing the pivot operation, one having a magnification adjustment function and/or an AF function may be used favorably as the imaging section 520. During the pivot operation, the distance f between the pivot point $X_f$ and the wrist point $X_w$ is kept fixed, but the distance f may be set every time the pivot operation is executed. Consequently, if the magnification and the focal point of the imaging section 520 are non-adjustable, a clear picture can be obtained only during the pivot operation at a predetermined distance f, and for this reason convenience cannot be said to be high for the surgeon. By having the imaging section 520 have a magnification adjustment function and/or an AF function, and by appropriately adjusting the magnification and/or focal point in accordance with the distance f, it becomes possible to photograph a predetermined site more clearly, even during pivot operations with different distances f, and convenience for the surgeon can be improved significantly.

The above describes the first embodiment.

2. Second Embodiment

A second embodiment of the present disclosure will be described. Note that in the second to fourth embodiments described below, only the arrangements of actuators and encoders in each joint section of the arm section are different from the first embodiment, and other items are similar to the first embodiment. Consequently, in the following description of the second to the fourth embodiments, the features that differ from the first embodiment will be described primarily, whereas detailed description of features that overlap with the first embodiment will be omitted.

(2-1. Configuration of System and Support Arm Apparatus)

Figure 4:
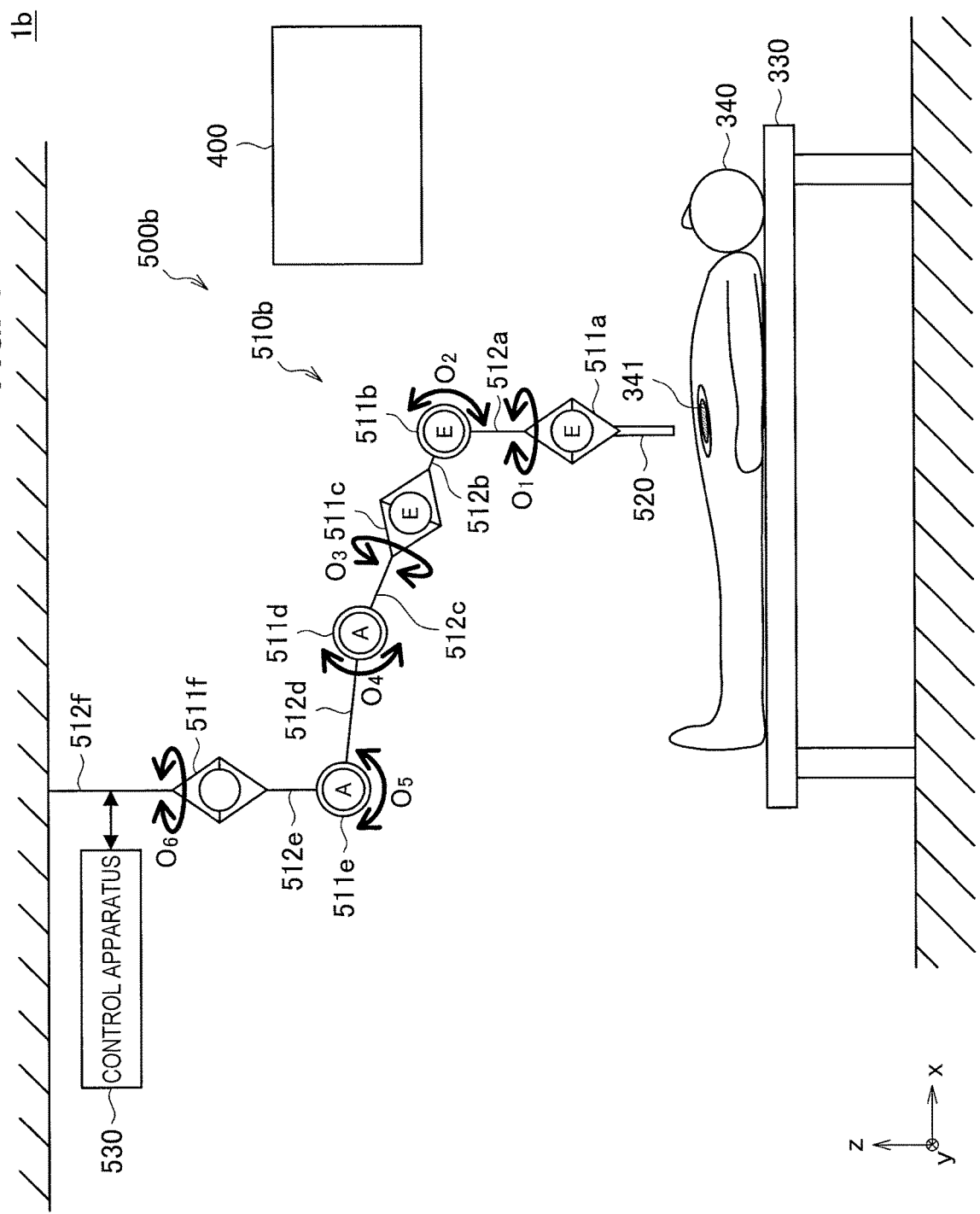
FIG. 4 is a diagram illustrating a schematic configuration of a medical system and a support arm apparatus according to a second embodiment.

Referring to FIG. 4, the configuration of the medical system and the support arm apparatus according to the second embodiment of the present disclosure will be described. FIG. 4 is a diagram illustrating a schematic configuration of the medical system and the support arm apparatus according to the second embodiment.

Referring to FIG. 4, the medical system $1b$ according to the second embodiment includes a support arm apparatus $500b$ and the display apparatus $400$. The configuration of the medical system $1b$ according to the second embodiment is similar to the medical system $1a$ according to the first embodiment described above, except that the configuration of the support arm apparatus $500b$ is different.

Referring to FIG. 4, the support arm apparatus $500b$ according to the second embodiment is provided with an arm section $510b$, the imaging section $520$ attached to the front end of the arm section $510b$, and the control apparatus $530$ that controls the operation of the support arm apparatus $500b$. The configuration of the support arm apparatus $500b$ is similar to the support arm apparatus $500a$ according to the first embodiment, except for the arrangement of the actuators and encoders provided in each of the joint sections $511a$ to $511f$ of the arm section $510b$.

In the second embodiment, in the arm section $510b$, among the rotation axes which are provided on the base end side and which may prescribe the position of the imaging section $520$, namely the fourth axis $O_4$ to the sixth axis $O_6$, the fourth axis $O_4$ and the fifth axis $O_5$ are configured as drive axes. In other words, actuators are provided in the joint sections $511d$ and $511e$ corresponding to these rotation axes.

Also, the rotation axes which are provided on the front end side and which may prescribe the attitude of the imaging section $520$, namely the first axis $O_1$ to the third axis $O_3$, are configured as passive axes. The joint sections $511a$ to $511c$ corresponding to these rotation axes are not provided with actuators, and are provided with encoders only.

Additionally, the sixth axis $O_6$ is also configured as a passive axis. However, the configuration of the joint section $511f$ corresponding to the sixth axis $O_6$ is arbitrary, and may be any type of configuration insofar as the sixth axis $O_6$ is made to function as a passive axis. For example, the joint section $511f$ may not be provided with any actuators or encoders.

Note that in FIG. 2, similarly to FIG. 1, the joint sections $511d$ and $511e$ provided with actuators are denoted with "A" and the joint sections $511a$ to $511c$ provided with encoders only are denoted with "E", thereby indicating the arrangement of the actuators and the encoders. Note that the arbitrarily configured joint section $511f$ is denoted with neither "A" nor "E", and is left blank.

According to the configuration, similarly to the first embodiment, by appropriately controlling the driving of the actuators provided in the joint sections $511d$ and $511e$ with the control apparatus $530$, the arm section $510b$ is capable of executing the gravity compensation operation. Since the details of the gravity compensation operation in the second embodiment are similar to the first embodiment, detailed description is omitted herein.

The above describes the second embodiment.

3. Third Embodiment (3-1. Configuration of System and Support Arm Apparatus)

Figure 5:
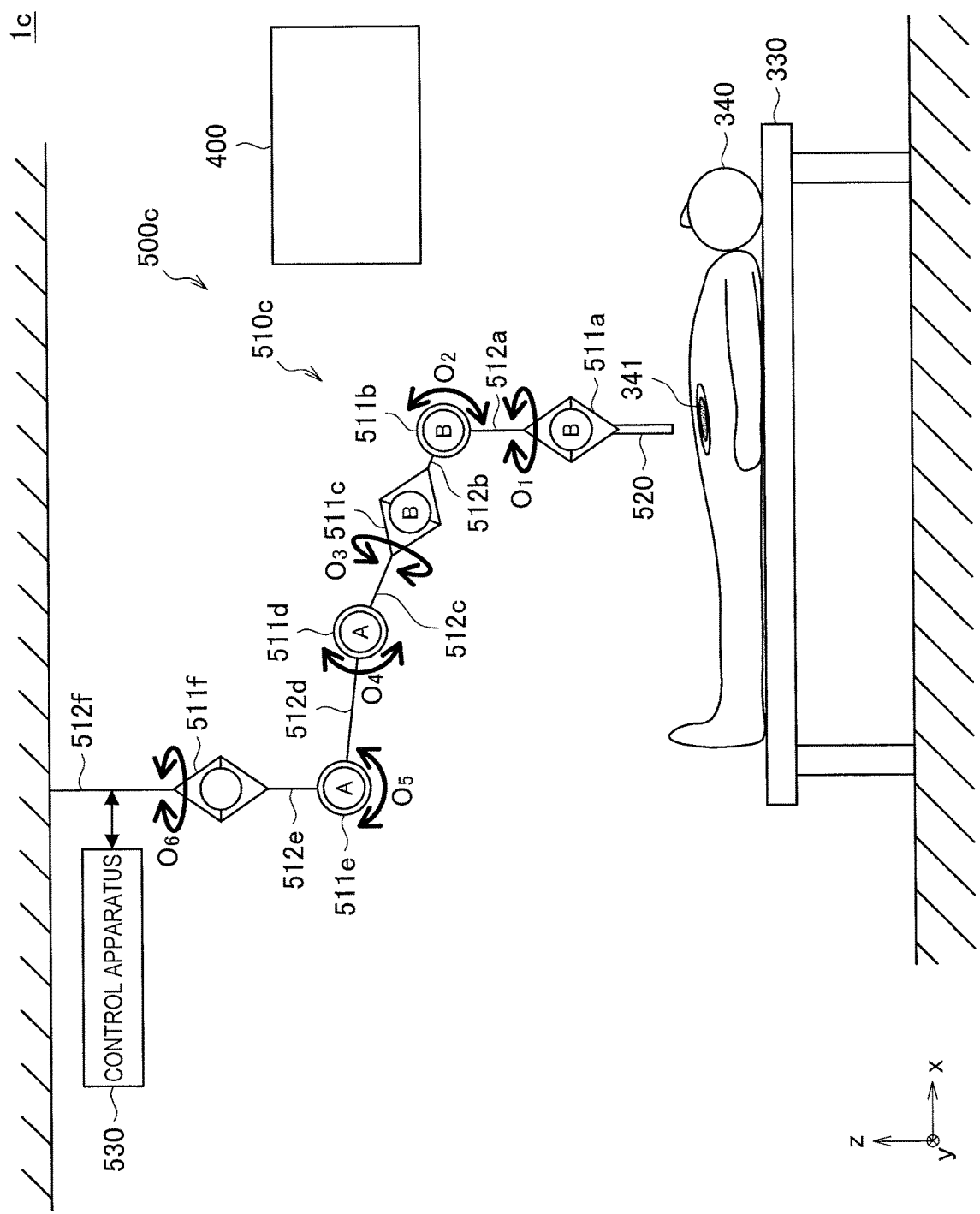
FIG. 5 is a diagram illustrating a schematic configuration of a medical system and a support arm apparatus according to a third embodiment.

Referring to FIG. 5, the configuration of the medical system and the support arm apparatus according to the third embodiment of the present disclosure will be described. FIG. 5 is a diagram illustrating a schematic configuration of the medical system and the support arm apparatus according to the third embodiment.

Referring to FIG. 5, the medical system $1c$ according to the third embodiment includes a support arm apparatus $500c$ and the display apparatus $400$. The configuration of the medical system $1c$ according to the third embodiment is similar to the medical system $1a$ according to the first embodiment described above, except that the configuration of the support arm apparatus $500c$ is different.

Referring to FIG. 5, the support arm apparatus $500c$ according to the third embodiment is provided with an arm section $510c$, the imaging section $520$ attached to the front end of the arm section $510c$, and the control apparatus $530$ that controls the operation of the support arm apparatus $500c$. The configuration of the support arm apparatus $500c$ is similar to the support arm apparatus $500a$ according to the first embodiment, except for the arrangement of the actuators and encoders provided in each of the joint sections $511a$ to $511f$ of the arm section $510c$.

In the third embodiment, in the arm section $510c$, among the rotation axes which are provided on the base end side and which may prescribe the position of the imaging section $520$, namely the fourth axis $O_4$ to the sixth axis $O_6$, the fourth axis $O_4$ and the fifth axis $O_5$ are configured as drive axes. In other words, actuators are provided in the joint sections $511d$ and $511e$ corresponding to these rotation axes.

Additionally, similarly to the second embodiment, the sixth axis $O_6$ is configured as a passive axis. The configuration of the joint section $511f$ corresponding to the sixth axis $O_6$ is arbitrary, and may be any type of configuration insofar as the sixth axis $O_6$ is made to function as a passive axis. For example, the joint section $511f$ may not be provided with any actuators or encoders.

Also, the rotation axes which are provided on the front end side and which may prescribe the attitude of the imaging section $520$, namely the first axis $O_1$ to the third axis $O_3$, are configured as passive axes. However, unlike the first and the second embodiments, the joint sections $511a$ to $511c$ corresponding to these rotation axes are not provided with any actuators or encoders. However, the configuration related to these joint sections $511a$ to $511c$ is configured so that balanced is achieved with the first axis $O_1$ to the third axis $O_3$, respectively. Herein, a state in which balance is achieved for a rotation axis means a state in which the center-of-gravity position of a movable section related to a rotation axis is aligned with the rotation axis, and even if the movable section rotates about the rotation axis, the center-of-gravity position does not change. In other words, the state is one in which the center-of-gravity position is fixed, regardless of changes in attitude.

Figure 6:
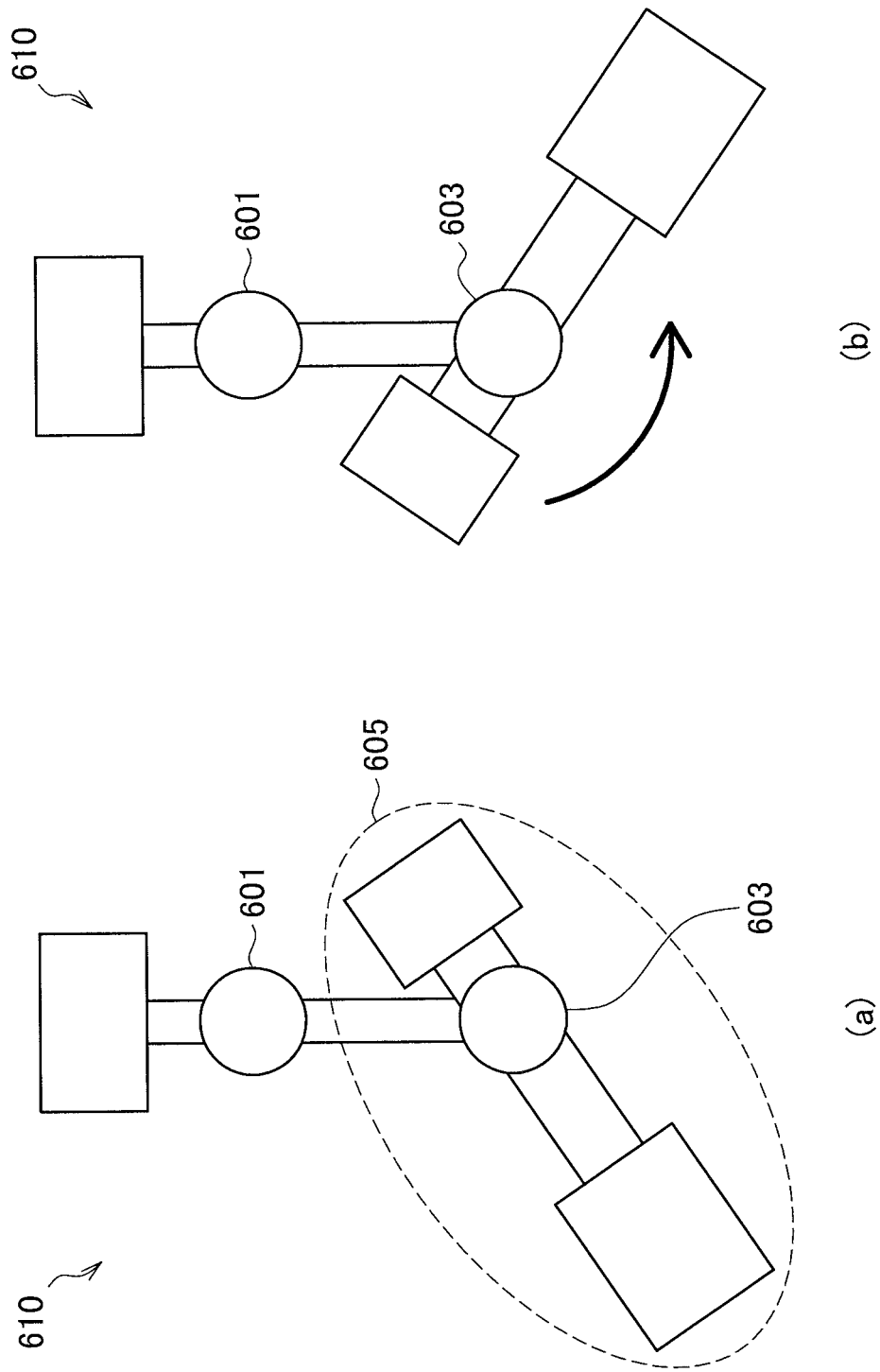
FIG. 6 is an explanatory diagram for explaining a state in which balance is achieved for a rotation axis.

FIG. 6 is an explanatory diagram for explaining a state in which balance is achieved for a rotation axis. In FIG. 6, for the sake of explanation, a simple arm section $610$ including two rotation axes is illustrated. The arm section $610$ is formed by a link connected by a joint section $601$ corresponding to the rotation axis of a first axis, and a joint section $603$ corresponding to the rotation axis of a second axis. A part $605$ enclosed by the dashed line in the drawing indicates the part that rotates in association with the rotation in the joint section $603$, or in other words, a movable section $605$ related to the rotation axis of the second axis.

For example, assume that the arm section $610$ is configured so that balance is achieved for the rotation axis of the second axis. In this case, the center-of-gravity position of the movable section $605$ is adjusted by a counterweight or the like, for example, so as to be aligned with the rotation axis of the second axis. When the center-of-gravity position is adjusted in this way, even if the movable section 605 rotates about the rotation axis of the second axis, like from the state illustrated in FIG. 6(a) to the state illustrated in FIG. 6(b), the center-of-gravity position of the movable section 605 is kept fixed. If the case in which the arm section 610 additionally includes a rotation axis of a third axis, if the movable section related to the rotation axis of the third axis is configured similarly so that balance is achieved for the rotation axis of the third axis, the center-of-gravity position of the movable section related to the rotation axis of the third axis does not change even if a rotation about the rotation axis of the third axis occurs. Consequently, effectively, both of the center-of-gravity positions of the movable section 605 related to the rotation axis of the second axis and the movable section related to the rotation axis of the third axis do not change.

Likewise in FIG. 5, similarly to FIG. 1 and the like, the joint sections 511d and 511e provided with actuators are denoted with "A", thereby indicating the arrangement of the actuators. Also, to indicate the rotation axes where balance is achieved, the corresponding joint sections 511a to 511c are denoted with "B". Note that the arbitrarily configured joint section 511f is denoted with neither "A" nor "B", and is left blank.

According to the configuration, similarly to the first and second embodiments, by appropriately controlling the driving of the actuators provided in the joint sections 511d and 511e with the control apparatus 530, the arm section 510c is capable of executing the gravity compensation operation. However, in the third embodiment, the processes performed by the control apparatus 530 during the gravity compensation operation are different from the first and second embodiments.

Specifically, in the third embodiment, with respect to the rotation axes on the front end side, namely the first axis $O_1$ to the third axis $O_3$, since the arm section 510c is configured so that balance is achieved for each of these rotation axes, the center-of-gravity position of the configuration on the front end side (the link 512c, the link 512c, the joint section 511c, the link 512b, the joint section 511b, the link 512a, the joint section 511a, and the imaging section 520) is fixed regardless of the attitude of the configuration on the front end side. Consequently, like the first and second embodiment, it is not necessary to perform a process of computing the center-of-gravity position on the basis of the detection values of the encoders.

In the third embodiment, information about the center-of-gravity position of the configuration on the front end side is input into the control apparatus 530. Consequently, on the basis of the information, the control apparatus 530 is able to calculate the moment imposed on the base end side by the configuration on the front end side, regardless of the attitude of the configuration on the front end side. By having the control apparatus 530 drive the actuators provided in the joint sections 511d and 511e so that a torque canceling out the calculated moment is generated, the gravity compensation operation is realized.

The above describes the third embodiment.

4. Fourth Embodiment (4-1. Configuration of System and Support Arm Apparatus)

Figure 7:
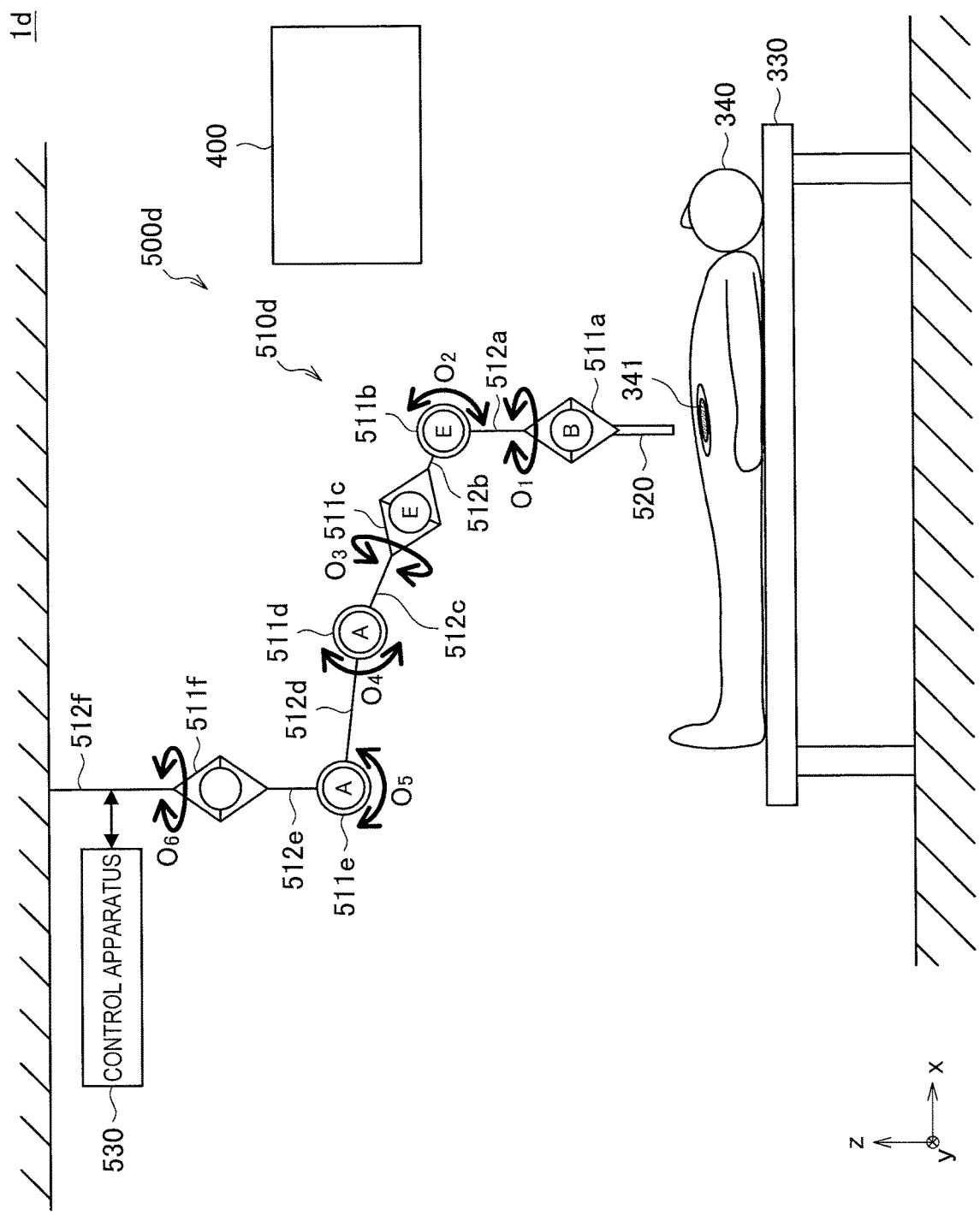
FIG. 7 is a diagram illustrating a schematic configuration of a medical system and a support arm apparatus according to a fourth embodiment.

Referring to FIG. 7, the configuration of the medical system and the support arm apparatus according to the fourth embodiment of the present disclosure will be described. FIG. 7 is a diagram illustrating a schematic configuration of the medical system and the support arm apparatus according to the fourth embodiment.

Referring to FIG. 7, the medical system 1d according to the fourth embodiment includes a support arm apparatus 500d and the display apparatus 400. The configuration of the medical system 1d according to the fourth embodiment is similar to the medical system 1a according to the first embodiment described above, except that the configuration of the support arm apparatus 500d is different.

Referring to FIG. 7, the support arm apparatus 500d according to the fourth embodiment is provided with an arm section 510d, the imaging section 520 attached to the front end of the arm section 510d, and the control apparatus 530 that controls the operation of the support arm apparatus 500d. The configuration of the support arm apparatus 500d is similar to the support arm apparatus 500a according to the first embodiment, except for the arrangement of the actuators and encoders provided in each of the joint sections 511a to 511f of the arm section 510d.

In the fourth embodiment, in the arm section 510d, among the rotation axes which are provided on the base end side and which may prescribe the position of the imaging section 520, namely the fourth axis $O_4$ to the sixth axis $O_6$, the fourth axis $O_4$ and the fifth axis $O_5$ are configured as drive axes. In other words, actuators are provided in the joint sections 511d and 511e corresponding to these rotation axes.

Also, the rotation axes which are provided on the front end side and which may prescribe the attitude of the imaging section 520, namely the first axis $O_1$ to the third axis $O_3$, are configured as passive axes. Of these, the joint sections 511b and 511c corresponding to the second axis $O_2$ and the third axis $O_3$ are provided with encoders. On the other hand, the joint section 511a corresponding to the first axis $O_1$ is not provided with an actuator or an encoder. However, the configuration according to the joint section 511a is configured so that balance is achieved for the first axis $O_1$.

Additionally, similarly to the second and third embodiments, the sixth axis $O_6$ is configured as a passive axis. The configuration of the joint section 511f corresponding to the sixth axis $O_6$ is arbitrary, and may be any type of configuration insofar as the sixth axis $O_6$ is made to function as a passive axis. For example, the joint section 511f may not be provided with any actuators or encoders.

Likewise in FIG. 7, similarly to FIG. 1 and the like, the joint sections 511d and 511e provided with actuators are denoted with "A" and the joint sections 511b and 511c provided with encoders are denoted with "E", thereby indicating the arrangement of the actuators and the encoders. Also, to indicate the rotation axis where balance is achieved, the corresponding joint section 511a is denoted with "B". Note that the arbitrarily configured joint section 511f is denoted with neither "A", "E", nor "B", and is left blank.

According to the configuration, similarly to the first to the third embodiments, by appropriately controlling the driving of the actuators provided in the joint sections 511d and 511e with the control apparatus 530, the arm section 510d is capable of executing the gravity compensation operation.

In the gravity compensation operation according to the fourth embodiment, by the encoders provided in the joint sections 511b and 511c, the rotational angles in the joint sections 511b and 511c are detected. On the basis of these detected rotational angles, the control apparatus 530 computes the current center-of-gravity position for the configuration related to the joint sections 511b and 511c from among the configuration on the front end side (that is, the link 512c, the joint section 511c, the link 512b, the joint section 511b, the link 512a, the joint section 511a, and the imaging section 520).

Also, with regard to the first axis $O_1$, since there is a configuration in which balance is achieved for the rotation axis, the center-of-gravity position of the configuration related to the first axis $O_1$ (that is, the configuration related to the joint section 511a) is fixed regardless of the attitude of the configuration. Information about the center-of-gravity position of the configuration related to the joint section 511a is input in advance into the control apparatus 530.

On the basis of the information about the center-of-gravity position of the configuration related to the joint sections 511b and 511c, and the information about the center-of-gravity position of the configuration related to the joint section 511a, the control apparatus 530 computes the center-of-gravity position of the configuration on the front end side, and on the basis of the center-of-gravity position of the configuration on the front end side, is able to calculate the moment imposed on the base end side by the configuration on the front end side. By having the control apparatus 530 drive the actuators provided in the joint sections 511d and 511e so that a torque canceling out the calculated moment is generated, the gravity compensation operation is realized.

The foregoing describes the fourth embodiment.

5. Fifth Embodiment

A fifth embodiment of the present disclosure will be described. Note that in the fifth to the seventh embodiments described below, only the structure of the arm section of the support arm apparatus is different from the first embodiment, and other items are similar to the first embodiment. Consequently, in the following description of the fifth to the seventh embodiments, the features that differ from the first embodiment will be described primarily, whereas detailed description of features that overlap with the first embodiment will be omitted.

(5-1. Configuration of System and Support Arm Apparatus)

Figure 8:
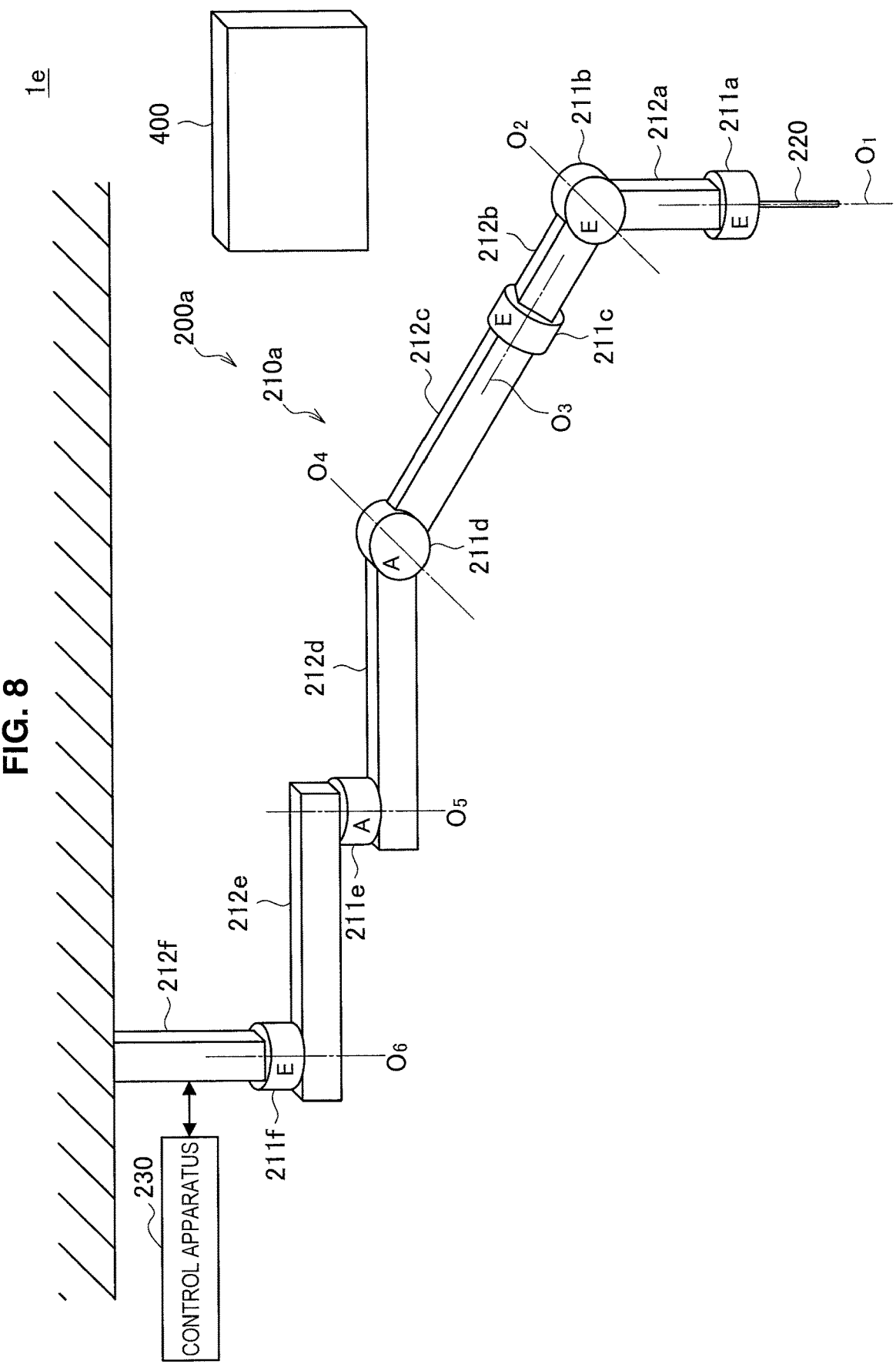
FIG. 8 is a diagram illustrating a schematic configuration of a medical system and a support arm apparatus according to a fifth embodiment.

Referring to FIG. 8, the configuration of the medical system and the support arm apparatus according to the fifth embodiment of the present disclosure will be described. FIG. 8 is a diagram illustrating a schematic configuration of the medical system and the support arm apparatus according to the fifth embodiment.

Referring to FIG. 8, the medical system 1e according to the fifth embodiment includes a support arm apparatus 200a and a display apparatus 400. The configuration of the medical system 1e according to the fifth embodiment is similar to the medical system 1a according to the first embodiment described above, except that the configuration of the support arm apparatus 200a is different.

Referring to FIG. 8, the support arm apparatus 200a according to the fifth embodiment is provided with an arm section 210a, an imaging section 220 attached to the front end of the arm section 210a, and a control apparatus 230 that controls the operation of the support arm apparatus 200a. Note that the imaging section 220 and the control apparatus 230 have a configuration and function similar to the imaging section 520 and the control apparatus 530 in the first embodiment.

The arm section 210a has a base end section attached to the ceiling of the operating room, and is installed to hang down from the ceiling. The arm section 210a includes joint sections 211a, 211b, 211c, 211d, 211e, and 211f respectively provided at positions corresponding to each rotation axis (called the first axis $O_1$, the second axis $O_2$, the third axis $O_2$, the fourth axis $O_4$, the fifth axis $O_5$, and the sixth axis $O_6$ in order from the front end side), and multiple links 212a, 212b, 212c, 212d, 212e, and 212f rotatably joined to each other by the joint sections 211b to 211f. Also, on the front end of the arm section 210a, the imaging section 220 is attached via the joint section 211a.

Note that in FIG. 8, the links 212a to 212f are illustrated as rod-shaped members having a rectangular cross-section, but the shape of the links 212a to 212f is not limited to such an example, and the cross-section may be any of various types of shapes, such as circular or elliptical. As a specific structure of the links 212a to 212f, any of various types used as the links of a typical support arm apparatus may be applied.

Also, although illustrated simply by cylinders in FIG. 8, in actuality, the joint sections 211a to 211f have shafts that act as rotation axes, bearings that pivotally support the shafts, and the like, and may be members enabling the rotation of one member about another member. However, similarly to each embodiment described above, the fifth embodiment likewise has a characteristic arrangement of actuators and encoders provided with respect to the joint sections 211a to 211f. In the fifth embodiment, it is sufficient for the joint sections 211a to 211f to be configured enabling the rotation of one member about another member, and also enabling the realization of the arrangement of the actuators and encoders described later, whereas for the rest of the specific structure, any of various types used as the joint sections of a typical support arm apparatus may be applied.

The configuration of the arm section 210a will be described in detail. The base end of the link 212f that extends in an approximately vertical direction is attached to the ceiling. The front end of the link 212f is joined to the base end of the link 212e through the joint section 211f, and the link 212f rotatably supports the link 212e through the joint section 211f.

Thereafter, similarly, the front ends of the links 212e, 212d, 212c, and 212b are joined to the base ends of the links 212d, 212c, 212b and 212a through the joint sections 211e, 211d, 211c, and 211b, respectively. In addition, the links 212e, 212d, 212c, and 212b rotatably support the links 212d, 212c, 212b, and 212a through the joint sections 211e, 211d, 211c, and 211b, respectively.

The imaging section 220 is joined to the front end of the link 212a through the joint section 211a. The link 212a rotatably supports the imaging section 220 through the joint section 211a.

In this way, the base end of the link 212f connected to the ceiling acts as a fulcrum, and ends of the multiple links 212a to 212f are joined to each other by the joint sections 211b to 211f, thereby forming an arm shape extending from the ceiling.

Herein, in the arm section 210a, among each of the rotation axes, for the first axis $O_1$ to the fourth axis $O_4$, the directions of the rotation axes are similar to the first embodiment. In other words, the first axis $O_1$ and the third axis $O_2$ are yaw axes, while the second axis $O_2$ and the fourth axis $O_4$ are pitch axes. On the other hand, in the arm section 210a, for the fifth axis $O_5$ and the sixth axis $O_6$, the directions of the rotation axes are different from the first embodiment.

In the arm section 210a, the fifth axis $O_5$ and the sixth axis $O_6$ both have rotation axes parallel to the vertical direction (z-axis direction). Additionally, the links 212d and 212e connected to the joint section 211e corresponding to the fifth axis $O_5$ and the joint section 211f corresponding to the sixth axis $O_6$ extend in an approximately horizontal direction. By rotation about the fifth axis $O_5$ and the sixth axis $O_6$, these links 212d and 212e rotate in the horizontal plane with one end as a base point.

In this way, the configuration related to the fifth axis $O_5$ and the sixth axis $O_6$ of the arm section 210a has what may be called a horizontal multi joint structure. By having a horizontal multi-joint structure, for example, even if by some chance an actuator related to the horizontal multi-joint structure malfunctions, only movement of the arm section 210a in the horizontal plane is brought about, and thus a situation in which the position of the front end of the arm section 210a moves greatly up and down can be avoided. Thus, it becomes possible to provide a safer medical system 1e.

In the fifth embodiment, in the arm section 210a, among the rotation axes which are provided on the base end side and which may prescribe the position of the imaging section 220, namely the fourth axis $O_4$ to the sixth axis $O_6$, the fourth axis $O_4$ and the fifth axis $O_5$ are configured as drive axes. In other words, actuators are provided in the joint sections 211d and 211e corresponding to these rotation axes.

Also, the rotation axes which are provided on the front end side and which may prescribe the attitude of the imaging section 220, namely the first axis $O_1$ to the third axis $O_3$, are configured as passive axes. The joint sections 211a to 211c corresponding to these rotation axes are not provided with actuators, and are provided with encoders only. Additionally, the sixth axis $O_6$ is also configured as a passive axis, and the joint section 211f corresponding to the rotation axis is provided with an encoder only.

Note that in FIG. 8, similarly to FIG. 1 and the like, the joint sections 211d to 211f provided with actuators are denoted with "A" and the joint sections 211a to 211c provided with encoders only are denoted with "E", thereby indicating the arrangement of the actuators and the encoders.

According to the configuration, by appropriately controlling the driving of the actuator provided in the joint section 211d with the control apparatus 230, the arm section 210a is capable of executing the gravity compensation operation.

Specifically, in the gravity compensation operation, the control apparatus 230 computes the center-of-gravity position of the configuration on the front end side (the link 212c, the joint section 211c, the link 212b, the joint section 211b, the link 212a, the joint section 211a, and the imaging section 220), on the basis of the rotational angles of the joint sections 211a to 211c detected by the encoders. Additionally, on the basis of the computed center-of-gravity position of the configuration on the front end side, the control apparatus 230 calculates the moment imposed on the base end side by the configuration on the front end side, and drives the actuator provided in the joint section 211d so that a torque canceling out the moment is generated.

The above describes the fifth embodiment.

6. Sixth Embodiment (6-1. Configuration of System and Support Arm Apparatus)

Figure 9:
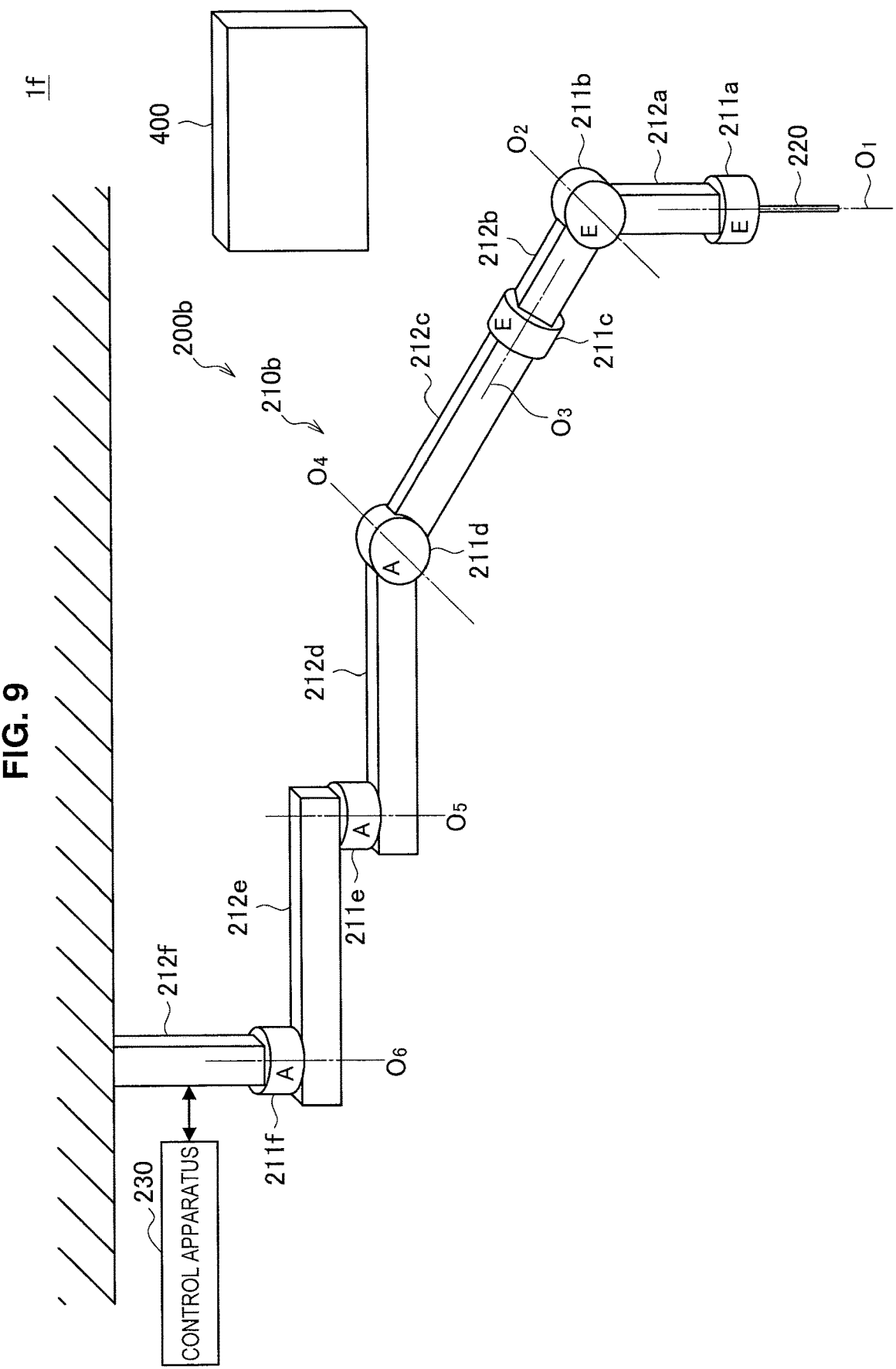
FIG. 9 is a diagram illustrating a schematic configuration of a medical system and a support arm apparatus according to a sixth embodiment.

Referring to FIG. 9, the configuration of the medical system and the support arm apparatus according to the sixth embodiment of the present disclosure will be described. FIG. 9 is a diagram illustrating a schematic configuration of the medical system and the support arm apparatus according to the sixth embodiment.

Referring to FIG. 9, the medical system 1f according to the sixth embodiment includes a support arm apparatus 200b and the display apparatus 400. The configuration of the medical system 1f according to the sixth embodiment is similar to the medical system 1a according to the first embodiment described above, except that the configuration of the support arm apparatus 200b is different.

Referring to FIG. 9, the support arm apparatus 200b according to the sixth embodiment is provided with an arm section 210b, the imaging section 220 attached to the front end of the arm section 210b, and a control apparatus 230 that controls the operation of the support arm apparatus 200b. The configuration of the support arm apparatus 200b is similar to the support arm apparatus 200a according to the fifth embodiment, except for the arrangement of the actuators and encoders provided in each of the joint sections 211a to 211f of the arm section 210b.

The arrangement of the actuators and encoders in the arm section 210b is similar to the first embodiment. In other words, in the sixth embodiment, among the first axis $O_1$ to the sixth axis $O_6$, the rotation axes which are provided on the base end side and which may prescribe the position of the imaging section 220, namely the fourth axis $O_4$ to the sixth axis $O_6$, are configured as drive axes. In other words, actuators are provided in the joint sections 211d to 211f corresponding to these rotation axes.

Also, the rotation axes which are provided on the front end side and which may prescribe the attitude of the imaging section 220, namely the first axis $O_1$ to the third axis $O_3$, are configured as passive axes. The joint sections 211a to 211c corresponding to these rotation axes are not provided with actuators, and are provided with encoders only.

Note that in FIG. 9, similarly to FIG. 1 and the like, the joint sections 211d to 211f provided with actuators are denoted with "A" and the joint sections 211a to 211c provided with encoders only are denoted with "E", thereby indicating the arrangement of the actuators and the encoders.

According to the configuration, by appropriately controlling the driving of the actuator provided in the joint section 211d with the control apparatus 230, the arm section 210b is capable of executing the gravity compensation operation. Also, according to the configuration, by appropriately controlling the driving of the actuators provided in the joint sections 211d to 211f with the control apparatus 230, the arm section 210b is capable of executing the position fine movement operation and the pivot operation.

In the gravity compensation operation, in the control apparatus 230, processes similar to the fifth embodiment are performed. Specifically, the control apparatus 230 computes the center-of-gravity position of the configuration on the front end side (the link 212c, the joint section 211c, the link 212b, the joint section 211b, the link 212a, the joint section 211a, and the imaging section 220), on the basis of the rotational angles of the joint sections 211a to 211c detected by the encoders. Additionally, on the basis of the computed center-of-gravity position of the configuration on the front end side, the control apparatus 230 calculates the moment imposed on the base end side by the configuration on the front end side, and drives the actuator provided in the joint section 211d so that a torque canceling out the moment is generated.

Also, in the position fine movement operation and the pivot operation, in the control apparatus 230, processes similar to the first embodiment are performed. Specifically, in the position fine movement operation, the control apparatus 230 drives the actuators provided in the joint sections 211d to 211f so that, in accordance with operation input by the surgeon, the imaging section 220 is translated in the direction corresponding to the operation input.

In the pivot operation, the rotational angles of the joint sections 211a to 211c decided in accordance with the operation of the surgeon are detected by the encoders, and from the detection values of the encoders and the pivot point to constrain, the control apparatus 230 computes the angles of the drive axes (the fourth axis $O_4$ to the sixth axis $O_6$) so as to realize the pivot operation. Additionally, in accordance with the angles, the control apparatus 230 drives the actuators provided in the joint sections 211d to 211f.

The above describes the sixth embodiment.

7. Seventh Embodiment (7-1. Configuration of System and Support Arm Apparatus)

Figure 10:
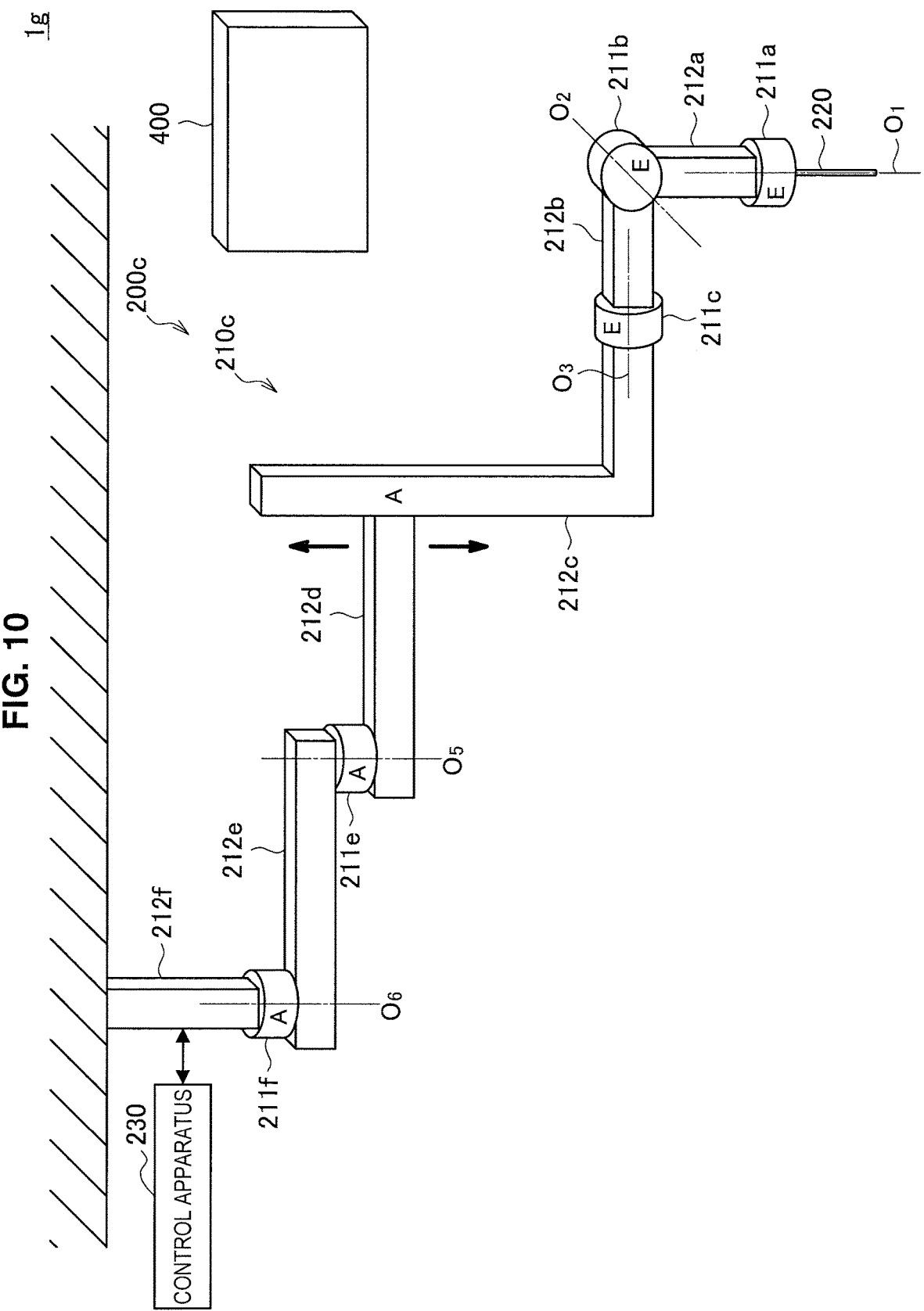
FIG. 10 is a diagram illustrating a schematic configuration of a medical system and a support arm apparatus according to a seventh embodiment.

Referring to FIG. 10, the configuration of the medical system and the support arm apparatus according to the seventh embodiment of the present disclosure will be described. FIG. 10 is a diagram illustrating a schematic configuration of a medical system and a support arm apparatus according to the seventh embodiment.

Referring to FIG. 10, the medical system 1g according to the seventh embodiment includes a support arm apparatus 200c and the display apparatus 400. The configuration of the medical system 1g according to the seventh embodiment is similar to the medical system 1a according to the first embodiment described above, except that the configuration of the support arm apparatus 200c is different.

Referring to FIG. 10, the support arm apparatus 200c according to the seventh embodiment is provided with an arm section 210c, the imaging section 220 attached to the front end of the arm section 210c, and a control apparatus 230 that controls the operation of the support arm apparatus 200a.

The arm section 210c according to the seventh embodiment has a configuration approximately similar to the arm section 210b according to the sixth embodiment. However, in the arm section 210c, a linear motion mechanism is provided instead of the joint section 211d corresponding to the fourth axis $O_4$.

Specifically, in the arm section 210c, the link 212c whose front end is connected to the joint section 211c corresponding to the third axis $O_3$ is configured to have an approximate L-shape, and is arranged so that the part corresponding to the short edge extends in an approximately horizontal direction, while the part corresponding to the long edge extends in an approximately vertical direction. The front end of the part corresponding to the short edge is connected to the joint section 211c. Additionally, on the face extending in the approximately vertical direction of the part corresponding to the long edge, the front end of the link 212d whose base end is connected to the joint section 211e corresponding to the fifth axis $O_5$ is connected so as to abut approximately vertically.

On the part corresponding to the long edge of the link 212c, on the face that abuts the front end of the link 212d, a guide mechanism such as a rail is formed in the long-edge direction, and the front end of the link 212d is joined to the guide mechanism. By the guide mechanism, it becomes possible for the configuration on the front end side from the link 212c to translate in the vertical direction with respect to the link 212d.

In this way, the arm section 210c according to the seventh embodiment corresponds to one in which the joint section 211d in the configuration of the arm sections 210a and 210b according to the fifth and sixth configurations described above has been substituted with a linear motion mechanism, or in other words, one in which the rotation axis (fourth axis $O_4$) has been substituted with a translation axis. Since the fourth axis $O_4$ is a pitch axis, that is, a rotation axis causing the configuration on the front end side of the fourth axis $O_4$ to rotate so as to move in the up-and-down direction, even if the fourth axis $O_4$ is substituted with a translation axis in the vertical direction, the arm section 210c can have six degrees of freedom similar to the arm sections 210a and 210b.

Note that in this specification, rotation axes and translation axes are collectively designated movable axes. In the first to the sixth embodiments described above, the arm sections 510a, 510b, 510c, 510d, 210a, and 210b are configured so that all of the movable axes are rotation axes, but like the seventh embodiment, even with the arm section 210c configured to have a mix of rotation axes and translation axes, the arm section 210c is appropriately configured to have at least six degrees of freedom, thereby making it possible to realize the gravity compensation operation and the like, similarly to the first to the sixth embodiments. In this way, in the present disclosure, it is sufficient for the arm section to be configured to have at least six degrees of freedom, and each movable axis in the arm section may be a rotation axis or a translation axis.

In the seventh embodiment, among the first axis $O_1$ to the third axis $O_3$, the fifth axis $O_5$, and the sixth axis $O_6$, the rotation axes which are provided on the base end side and which may prescribe the position of the imaging section 220, namely the fifth axis $O_5$ and the sixth axis $O_6$, are configured as drive axes. In other words, actuators are provided in the joint sections 211e and 211f corresponding to these rotation axes.

Also, the translation axis corresponding to the linear motion mechanism fulfills the role of the fourth axis $O_4$, and the translation axis is also a movable axis that may prescribe the position of the imaging section 220. In the seventh embodiment, the translation axis is also configured as a drive axis. In other words, the linear motion mechanism corresponding to the translation axis is also provided with an actuator. The actuator causes the configuration on the front end side from the link 212c to translate in the vertical direction with respect to the link 212d. Also, the actuator may also be provided with an encoder, and the encoder is a linear encoder that detects the translation distance of the configuration on the front end side from the link 212c.

Also, the rotation axes which are provided on the front end side and which may prescribe the attitude of the imaging section 220, namely the first axis $O_1$ to the third axis $O_3$, are configured as passive axes. The joint sections 211a to 211c corresponding to these rotation axes are not provided with actuators, and are provided with encoders only. In this way, although different in that the fourth axis $O_4$ has been substituted with a translation axis, the arrangement of actuators and encoders in the arm section 210c is similar to the arm section 210b according to the sixth embodiment.

Note that in FIG. 10, similarly to FIG. 1 and the like, the joint sections 211d to 211f and the linear motion mechanism provided with actuators are denoted with "A" and the joint sections 211a to 211c provided with encoders only are denoted with "E", thereby indicating the arrangement of the actuators and the encoders.

According to the configuration, by appropriately controlling the driving of the actuator provided in the linear motion mechanism with the control apparatus 230, the arm section 210c is capable of executing the gravity compensation operation. Also, according to the configuration, by appropriately controlling the driving of the actuators provided in the joint sections 211e and 211f and the actuator provided in the linear motion mechanism with the control apparatus 230, the arm section 210a is capable of executing the position fine movement operation and the pivot operation.

In the gravity compensation operation, the position fine movement operation and the pivot operation, in the control apparatus 230, processes similar to the sixth embodiment are performed. Specifically, in the gravity compensation operation, the control apparatus 230 computes the center-of-gravity position of the configuration on the front end side (the link 212c, the joint section 211c, the link 212b, the joint section 211b, the link 212a, the joint section 211a, and the imaging section 220), on the basis of the rotational angles of the joint sections 211a to 211c detected by the encoders. Additionally, on the basis of the computed center-of-gravity position of the configuration on the front end side, the control apparatus 230 calculates the moment imposed on the base end side by the configuration on the front end side, and drives the actuator provided in the linear motion mechanism so that a torque canceling out the moment is generated.

In the position fine movement operation, the control apparatus 230 drives the actuators provided in the joint sections 211e and 211f and the actuator provided in the linear motion mechanism so that, in accordance with operation input by the surgeon, the imaging section 220 is translated in the direction corresponding to the operation input.

In the pivot operation, the rotational angles of the joint sections 211a to 211c decided in accordance with the operation of the surgeon are detected by the encoders, and from the detection values of the encoders and the pivot point to constrain, the control apparatus 230 computes the change amounts of the drive axes (that is, the movement distance of the translation axis and the rotational angles of the fifth axis $O_5$ and the sixth axis $O_6$) so as to realize the pivot operation. Additionally, in accordance with the change amounts, the control apparatus 230 drives the actuators provided in the joint sections 211e and 211f and the actuator provided in the linear motion mechanism.

The above describes the seventh embodiment.

8. Conclusion

The first to the seventh embodiments described above will be summarized.

As described above, in all of the support arm apparatus 500a, 500b, 500c, 500d, 200a, 200b, and 200c according to the first to the seventh embodiments, the gravity compensation operation is executable. With this arrangement, even without providing a counterweight, the arm sections 510a 510b 510c 510d, 210a, 210b, and 210c become able to maintain their position and attitude. Consequently, a more compact and lightweight support arm apparatus 500a, 500b, 500c, 500d, 200a, 200b, and 200c may be realized, without impairing operability for the surgeon. Thus, relatively easy installation becomes possible, without occupying space inside the operating room, and also even in the case of configuring the arm sections 510a, 510b, 510c, 510d, 210a, 210b, and 210c to hang down from the ceiling as illustrated.

Also, in the support arm apparatus 500a, 500b, 500c, 500d, 200a, 200b, and 200c, since the driving of the arm sections 510a, 510b, 510c, 510d, 210a, and 210c is performed by actuators, by driving the arm sections 510a, 510b, 510c, 510d, 210a, 210b, and 210c with actuators to assist with the inertial component, fast and comfortable operation becomes possible compared to what is called a balance arm provided with a counterweight.

Herein, as a method for maintaining the position and the attitude of an arm section without providing a counterweight, a method of providing actuators in all of the joint sections of the arm section (that is, a method of configuring all of the rotation axes as drive axes) is also conceivable. However, with such a configuration, many actuators become necessary, and the costs increase greatly. Also, since actuators are also disposed in the joint sections near the front end of the arm section, the configuration near the front end becomes bulkier and heavier. If the configuration near the front end becomes bulkier, the field of view of the surgeon observing the photographed picture and the work space of the surgeon become impeded by the configuration near the front end, and there is a risk of creating an impediment to the smooth execution of surgery.

On the other hand, in the support arm apparatus 500a, 500b, 500c, 500d, 200a, 200b, and 200c, actuators are provided only in some of the joint sections. Consequently, costs can be reduced compared to a configuration in which actuators are provided in all of the joint sections as above. Also, in the support arm apparatus 500a, 500b, 500c, 500d, 200a, 200b, and 200c, the joint sections provided with actuators may be joint sections relatively on the base end side (for example, the joint sections 511a, 511b, 511c, 211a, 211b, and 211c which may prescribe the position of the imaging sections 520 and 220). Thus, the configuration near the front end can be miniaturized, making it possible to secure the field of view of the surgeon and the work space of the surgeon more easily.

Furthermore, in the support arm apparatus 500a, 200b, and 200c according to the first, sixth, and seventh embodiments, in addition to the gravity compensation operation, the position fine movement operation and the pivot operation are also executable. In this way, according to these support arm apparatus 500a, 200b, and 200c, it becomes possible to stay compact while also executing operations that further raise convenience for the surgeon, such as the position fine movement operation and the pivot operation.

9. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

For example, in the above embodiments, the medical support arm apparatus 500a, 500b, 500c, 500d, 200a, 200b, and 200c are described, but the present technology is not limited to such an example. For example, the support arm apparatus 500a, 500b, 500c, 500d, 200a, 200b, and 200c according to each embodiment described above may also be used for industrial uses, such as manufacturing steps and inspection steps of a product at a factory.

Additionally, the present technology may also be configured as below.

(1)

A medical support arm apparatus including:

an arm section configured so that a medical tool is provided on a front end, and movable axes are arranged so that the arm section has at least six degrees of freedom, in which among the movable axes, a movable axis provided on the front end side that prescribes an attitude of the medical tool is a passive axis that rotates by following an external force, and at least one axis provided on a base end side that prescribes a position of the medical tool is a drive axis driven by an actuator.

(2)

The medical support arm apparatus according to (1), in which the drive axis is driven to perform a gravity compensation operation that supports a weight of a configuration farther on the front end side than the drive axis.

(3)

The medical support arm apparatus according to (2), in which a movable axis provided farther on the front end side than the drive axis is provided with an encoder that detects a change amount in the movable axis, and the drive axis is driven to perform the gravity compensation operation, on a basis of a center-of-gravity position of the configuration farther on the front end side than the drive axis, the center-of-gravity position being computed using a detection value of the encoder.

(4)

The medical support arm apparatus according to (2), in which the configuration farther on the front end side than the drive axis is configured so that a center-of-gravity position is fixed regardless of changes in attitude, and the drive axis is driven to perform the gravity compensation operation on a basis of the center-of-gravity position.

(5)

The medical support arm apparatus according to any one of (1) to (4), in which among six movable axes corresponding to the six degrees of freedom of the arm section, three movable axes on the base end side are drive axes, and three movable axes on the front end side are passive axes, each of the three movable axes which are passive axes is provided with an encoder that detects a change amount in the movable axis, and the drive axes are driven to perform a pivot operation in which the medical tool moves in a state in which the medical tool is facing a predetermined point in space, and a distance to the predetermined point is kept fixed.

(6)

The medical support arm apparatus according to any one of (1) to (5), in which among six movable axes corresponding to the six degrees of freedom of the arm section, three movable axes on the base end side are drive axes, and three movable axes on the front end side are passive axes, each of the three movable axes which are passive axes is provided with an encoder that detects a change amount in the movable axis, and the drive axes are driven to perform a fine movement operation that causes the medical tool to move finely in a direction in accordance with a user operation.

(7)

The medical support arm apparatus according to any one of (1) to (6), in which the arm section includes a horizontal multi-joint structure.

(8)

The medical support arm apparatus according to any one of (1) to (7), in which at least one of the movable axes provided in the arm section is a translation axis indicating an axis that causes one link to be translated in a predetermined direction with respect to another link.

(9)

The medical support arm apparatus according to any one of (1) to (8), in which the medical tool is an imaging section that takes an image of an operating site.

(10)

The medical support arm apparatus according to (9), in which the imaging section has an AF function.

(11)

A medical system including:

an observation apparatus configured to take an image of an operating site for observing the operating site; and a display apparatus configured to display the taken image, in which the observation apparatus includes an arm section configured so that an imaging section that takes the image is provided on a front end, and movable axes are arranged so that the arm section has at least six degrees of freedom, and in the arm section, among the movable axes of the arm section, a movable axis provided on the front end side that prescribes an attitude of the imaging section is a passive axis that rotates by following an external force, and at least one axis provided on a base end side that prescribes a position of the imaging section is a drive axis driven by an actuator.

REFERENCE SIGNS LIST 1a, 1b, 1c, 1d, 1e, 1f, 1g medical system
400 display apparatus
500a, 500b, 500c, 500d, 200a, 200b, 200c support arm apparatus
510a, 510b, 510c, 510d, 210a, 210b, 210c arm section
511a, 511b, 511c, 511d, 511e, 511f, 211a, 211b, 211c, 211d, 211e, 211f joint section
512a, 512b, 512c, 512d, 512e, 512f, 212a, 212b, 212c, 212d, 212e, 212f link
520, 220 imaging section
530, 230 control apparatus

The invention claimed is:

1. A medical support arm apparatus comprising:
an arm section, having a base end and a front end, configured so that a medical tool is provided on the front end, the arm section having at least six movable axes, including a distal-most axis, a second distal-most axis, a third distal-most axis, a third proximal-most axis, a second proximal-most axis, and a proximal-most axis in this order from the front end to the base end, so that the arm section has at least six degrees of freedom, the distal-most axis being located at the front end of the arm section and the proximal-most axis being located at the base end of the arm; and
processing circuitry configured to control the arm section, wherein
the proximal-most axis, the second proximal-most axis, and the third proximal-most axis are drive axes driven by a first actuator, a second actuator, and a third actuator provided to the proximal-most axis, the second proximal-most axis, and the third proximal-most axis respectively, the distal-most axis, the second distal-most axis, and the third distal-most axis, corresponding to a wrist section of the arm section, are passive axes that rotate by following an external force, the distal-most axis, the second distal-most axis, and the third distal-most axis are provided with a first encoder, a second encoder, and a third encoder for detecting a rotation angle of the distal-most axis, the second distal-most axis, and the third distal-most axis respectively, and the processing circuitry is configured to drive the drive axes to perform a pivot operation in which the medical tool moves in a state in which the medical tool is facing a predetermined pivot point in space, and a distance to the predetermined pivot point is kept fixed, by:

obtaining, from the first encoder, the second encoder, and the third encoder, the rotation angle of the distal-most axis, the second distal-most axis, and the third distal-most axis respectively, determining an attitude vector of the wrist section corresponding to the distal-most axis, the second distal-most axis, and the third distal-most axis, indicating an attitude of the wrist section, based on the rotation angles of the distal-most axis, the second distal-most axis, and the third distal-most axis, determining a wrist point $X_w$, indicating a center-of-gravity of the wrist section corresponding to the distal-most axis, the second distal-most axis, and the third distal-most axis, based on the predetermined pivot point and the determined attitude vector, determining a rotation angle of each of the proximal-most axis, the second proximal-most axis, and the third proximal-most axis that realizes the determined wrist point $X_w$, and controlling the first actuator, the second actuator, and the third actuator to drive the proximal-most axis, the second proximal-most axis, and the third proximal-most axis respectively in accordance with each of the determined rotation angle of the proximal-most axis, the second proximal-most axis, and the third proximal-most axis respectively.

2. The medical support arm apparatus according to claim 1, wherein
the drive axes are driven to perform a gravity compensation operation that supports a weight of the wrist section.

3. The medical support arm apparatus according to claim 2, wherein
the wrist section is configured so that the wrist point $X_w$ is fixed regardless of changes in attitude.

4. The medical support arm apparatus according to claim 1, wherein
the drive axes are driven to perfo a fine movement operation that causes the medical tool to move finely in a direction in accordance with a user operation.

5. The medical support arm apparatus according to claim 1, wherein
the arm section includes a horizontal multi-joint structure.

6. The medical support arm apparatus according to claim 1, wherein
at least one of the movable axes provided in the arm section is a translation axis indicating an axis that causes one link to be translated in a predetermined direction with respect to another link.

7. The medical support arm apparatus according to claim 1, wherein
the medical tool is an imaging section that takes an image of an operating site.

8. The medical support arm apparatus according to claim 7, wherein
the imaging section has an autofocus (AF) function.

9. A medical system comprising:
an observation apparatus configured to take an image of an operating site for observing the operating site; and
a display apparatus configured to display the taken image, wherein
the observation apparatus includes
an arm section, having a base end and a front end, configured so that an imaging section that takes the image is provided on a front end, the arm section having at least six movable axes, including a distal-most axis, a second distal-most axis, a third distal-most axis, a third proximal-most axis, a second proximal-most axis, and a proximal-most axis in this order from the front end to the base end, so that the arm section has at least six degrees of freedom, the distal-most axis being located at the front end of the arm section and the proximal-most axis being located at the base end of the arm, and
processing circuitry configured to control the arm section,
the proximal-most axis, the second proximal-most axis, and the third proximal-most axis are drive axes driven by a first actuator, a second actuator, and a third actuator provided to the proximal-most axis, the second proximal-most axis, and the third proximal-most axis respectively,
the distal-most axis, the second distal-most axis, and the third distal-most axis, corresponding to a wrist section of the aifu section, are passive axes that rotate by following an external force,
the distal-most axis, the second distal-most axis, and the third distal-most axis are provided with a first encoder, a second encoder, and a third encoder for detecting a rotation angle of the distal-most axis, the second distal-most axis, and the third distal-most axis respectively, and
the processing circuitry is configured to drive the drive axes to perform a pivot operation in which the medical tool moves in a state in which the medical tool is facing a predetermined pivot point in space, and a distance to the predetermined pivot point is kept fixed, by:
obtaining, from the encoder the first encoder, the second encoder, and the third encoder, the rotation angle of the distal-most axis, the second distal-most axis, and the third distal-most axis respectively,
determining an attitude vector of the wrist section corresponding to the distal-most axis, the second distal-most axis, and the third distal-most axis, indicating an attitude of the wrist section, based on the rotation angles of the distal-most axis. the second distal-most axis, and the third distal-most axis,
determining a wrist point $X_w$, indicating a center-of-gravity of the wrist section corresponding to the distal-most axis, the second distal-most axis, and the third distal-most axis, based on the predetermined pivot point and the determined attitude vector,
determining a rotation angle of each of the proximal-most axis, the second proximal-most axis, and the third proximal-most axis that realizes the determined wrist point $X_w$, and controlling the first actuator, the second actuator, and the third actuator to drive the proximal-most axis, the second proximal-most axis, and the third proximal-most axis respectively in accordance with each of the determined rotation angle of the proximal-most axis, the second proximal-most axis, and the third proximal-most axis respectively.

* * * * *